US 6,618,144 B1

(12) United States Patent
Reed

(10) Patent No.: US 6,618,144 B1
(45) Date of Patent: Sep. 9, 2003

(54) DEVICE AND METHOD OF SIMULTANEOUSLY MEASURING THE LIGHT SCATTERING FROM MULTIPLE LIQUID SAMPLES CONTAINING POLYMERS AND/OR COLLOIDS

(75) Inventor: Wayne F. Reed, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 0 days.

(21) Appl. No.: 09/690,099

(22) Filed: Oct. 16, 2000

Related U.S. Application Data

(60) Provisional application No. 60/159,839, filed on Oct. 15, 1999.

(51) Int. Cl.[7] ............................................. G01N 21/00
(52) U.S. Cl. .................... 356/343; 356/336; 356/337
(58) Field of Search ............................ 356/335–343, 356/39–41, 432, 433, 435, 439, 440, 441; 250/574, 575; 422/82.08, 82.09

(56) References Cited

U.S. PATENT DOCUMENTS

| | | | |
|---|---|---|---|
| 3,809,912 A | 5/1974 | Henning | |
| 4,541,719 A | 9/1985 | Wyatt | |
| 4,639,137 A | * 1/1987 | Hazan et al. | 356/339 |
| 4,784,486 A | * 11/1988 | Van Wagenen et al. | 356/301 |
| 5,011,286 A | 4/1991 | Petralli | |
| 5,015,867 A | * 5/1991 | Siegel et al. | 250/560 |
| 5,162,863 A | * 11/1992 | Ito | 356/336 |
| 5,185,641 A | 2/1993 | Igushi et al. | |
| 5,255,072 A | 10/1993 | Mikasa et al. | |
| 5,293,210 A | 3/1994 | Berndt | |
| 5,426,501 A | * 6/1995 | Hokanson et al. | 356/335 |
| 5,427,920 A | 6/1995 | Berndt et al. | |
| 5,683,661 A | * 11/1997 | Hearst et al. | 442/186.3 |
| 5,907,399 A | 5/1999 | Shirasawa et al. | |
| 6,052,184 A | 4/2000 | Reed | |
| 6,075,610 A | * 6/2000 | Ueda et al. | 356/343 |
| 6,118,531 A | 9/2000 | Hertel et al. | |
| 6,118,532 A | 9/2000 | Peters | |
| 6,139,800 A | * 10/2000 | Chandler | 356/72 |
| 6,228,652 B1 | * 5/2001 | Rodriguez et al. | 356/336 |

OTHER PUBLICATIONS

Reed, Wayne F., "Data evaluation for unified multi-detector size exclusion chromatography—molar mass, viscosity and radius of gyration distributions" Macromol. Chem. Phys. 196, 1539–1575 (1995).

* cited by examiner

Primary Examiner—Frank G. Font
Assistant Examiner—Sang H. Nguyen
(74) Attorney, Agent, or Firm—Garvey, Smith, Nehrbass & Doody, L.L.C.; Seth M. Nehrbass

(57) ABSTRACT

Apparatus (10) for simultaneous light scattering includes a plurality of chambers and/or sub-chambers (41) in which light scattering can occur; a light source (20) or light sources for providing light to be scattered to the sub-chambers; light detectors (55, 62) optically coupled to the sub-chambers (41) for detecting scattered light; transmitters (31, 32) for transmitting information from the light detectors to a computer (30) for analysis. A method of performing simultaneous light scattering includes: providing a plurality of sub-chambers (41) in which light scattering can occur; providing light (22) to be scattered to the sub-chambers (41); detecting light scattered in the sub-chambers (41) with light detectors (55, 62); transmitting information from the light detectors (55, 62) to a computer (30) for analysis. Preferably, the information is transmitted to a single computer.

82 Claims, 6 Drawing Sheets

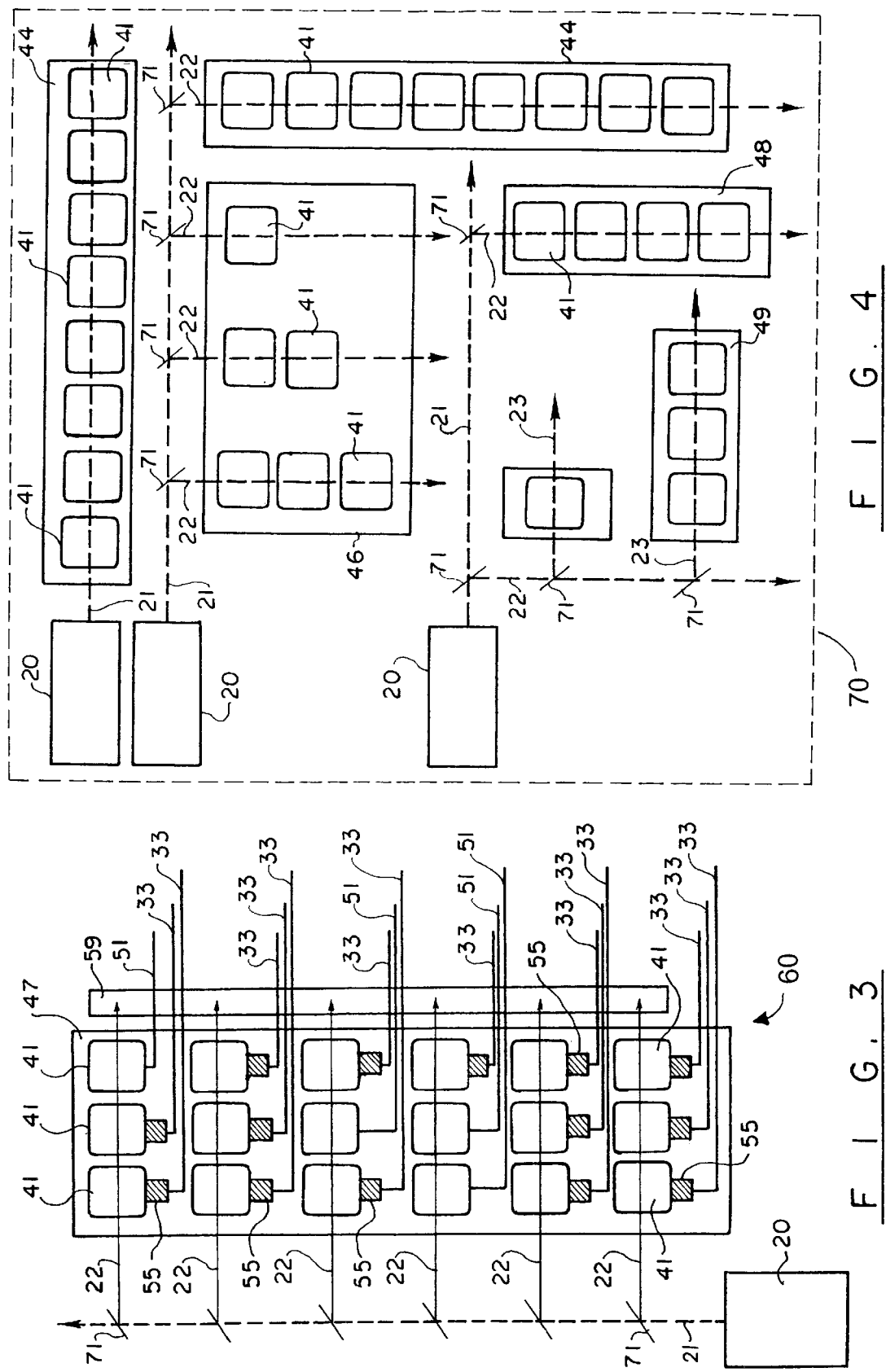

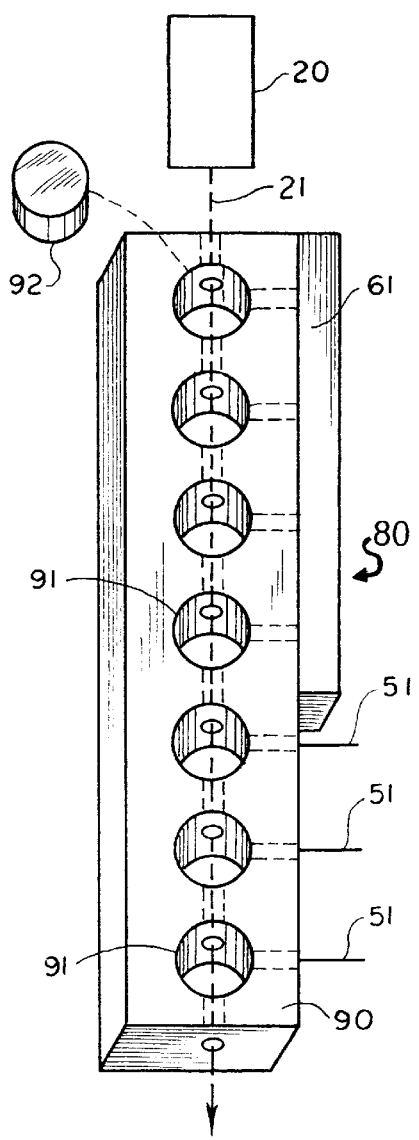
F I G . 5
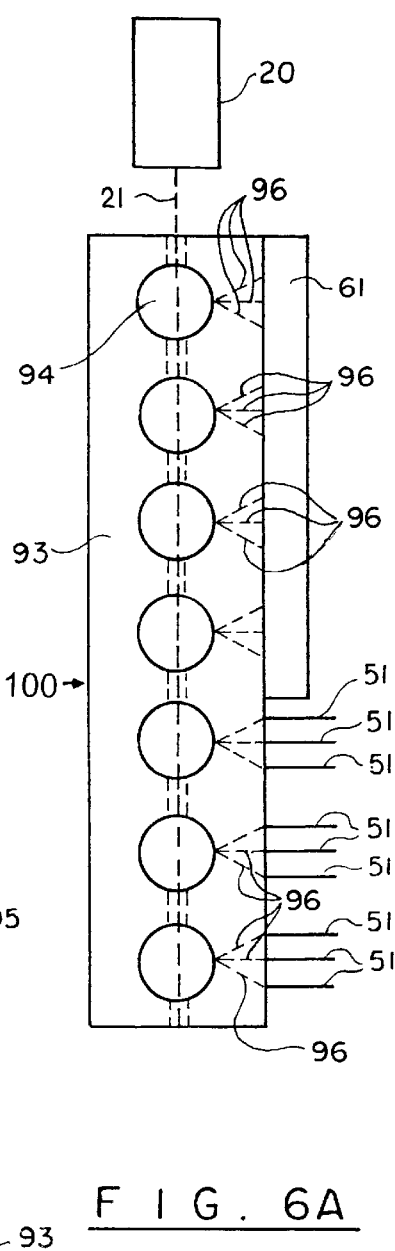
F I G . 6A
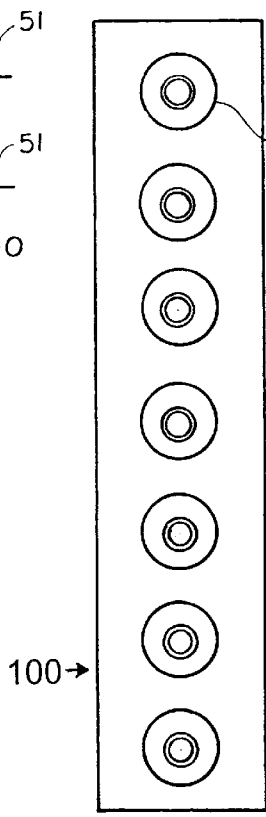
F I G . 6B

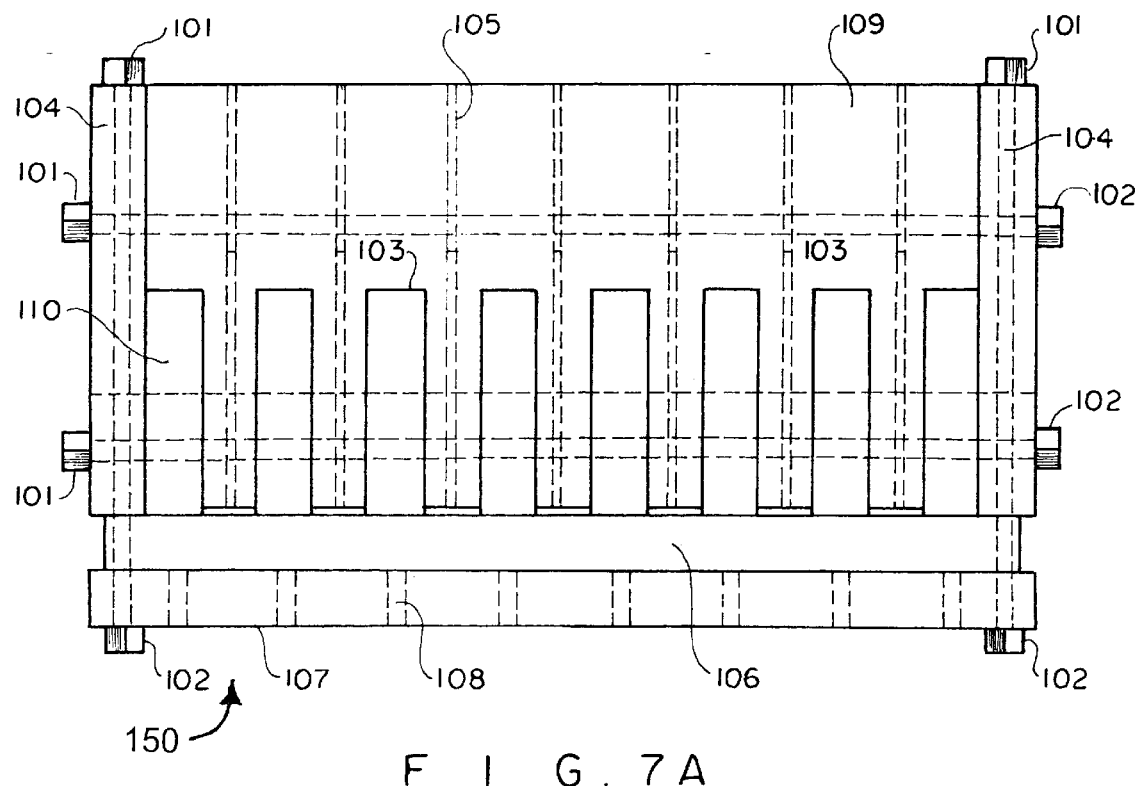
F I G. 7A
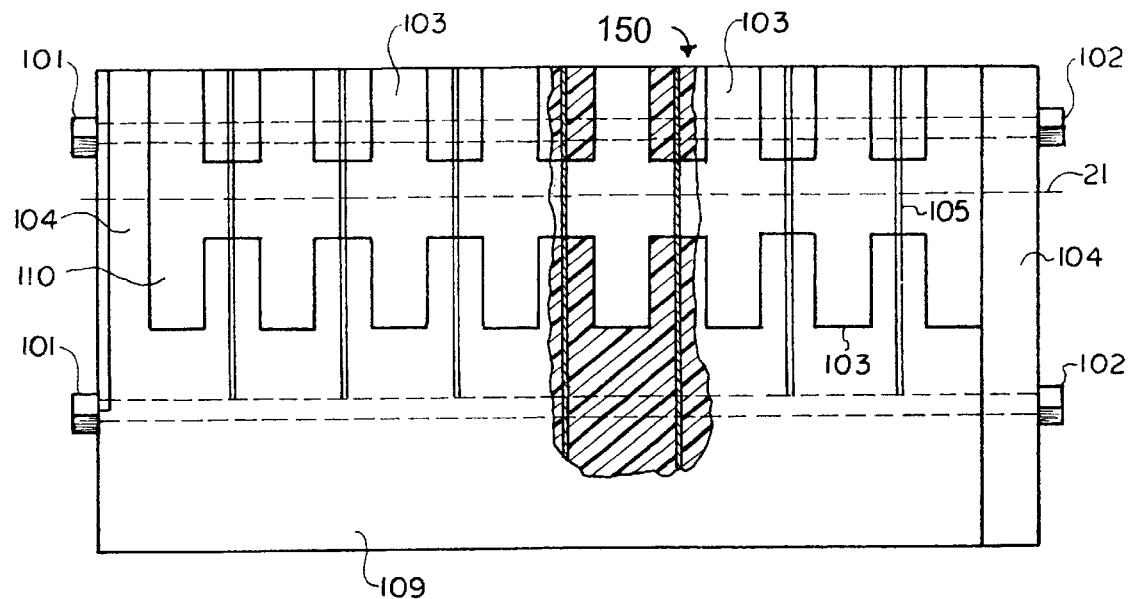
F I G. 7B

DEVICE AND METHOD OF SIMULTANEOUSLY MEASURING THE LIGHT SCATTERING FROM MULTIPLE LIQUID SAMPLES CONTAINING POLYMERS AND/OR COLLOIDS

CROSS-REFERENCE TO RELATED APPLICATIONS

My U.S. Provisional Patent Application Serial No. 60/159,839, filed Oct. 15, 1999, is incorporated herein by reference. Priority of that application is claimed.

My U.S. patent application Ser. No. 09/404,484, filed Sep. 23, 1999, is incorporated herein by reference.

My U.S. Pat. No. 6,052,184 is incorporated herein by reference.

My U.S. Provisional Patent Application Serial No. 60/031,095, filed Nov. 13, 1996, is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention involves the simultaneous measurement of light scattering from multiple, independent samples, comprising solutions containing polymers and/or colloids.

2. General Background of the Invention

The following patents are incorporated herein by reference:

U.S. Pat. Nos.: 3,809,912; 4,541,719; 5,011,286; 5,185,641; 5,255,072; 5,427,920; 5,907,399; 6,118,531; and 6,118,532.

U.S. Pat. No. 5,427,920 discloses multiple fluid compartments, each with its own light source and light detector.

U.S. Pat. No. 5,011,286 discloses a multisensor particle counter using a single beam to measure several fluid sample portions simultaneously.

U.S. Pat. No. 5,255,072 discloses using a single sensor to measure several fluids simultaneously.

SUMMARY OF THE INVENTION

The present invention comprises Simultaneous Multi-Sample Light Scattering, or SMSLS, for absolute and relative characterization of dilute macromolecular/colloidal solutions. Dilute here means that for a light beam incident on the solution the majority of scattering events are single scattering events. (Herein, 'single scattering' will refer to the case of light scattering in a solution wherein the majority of detected, scattered photons have scattered only once.) In prior art, light scattering devices have been made to measure only one sample at a time. This is in large part due to the fact that great care and expense has been taken to produce high quality optical cells for single samples, and it has not been obvious to practitioners that multiple independent measurements might be economically or technically feasible. Current art has also not taken account of the fact that significant advantages exist for being able to simultaneously measure the light scattered from multiple, independent samples. For convenience, the invention will be referred to herein as Simultaneous Multi-Sample Light Scattering, or SMSLS.

Emerging needs in new fields of polymer/colloid science and application now make such a multi-sampling capability extremely desirable. The following is a non-exhaustive list of fields in which multi-sampling will be of great utility:

1) Light scattering art has reached the phase where processes occurring in polymer/colloid solutions can be followed online.[1] At the industrial level, where large reactors are to be monitored, there is often considerable inhomogeneity within the reactor, so that samples withdrawn from different locations in the reactor can have different characteristics. Continuous and multi-stage reactors are other examples where SMSLS may be advantageous. The SMSLS invention will allow multiple samples withdrawn from different reactor locations to be characterized simultaneously, with a single device and computer. In prior art, the expense involved in using multiple, single sample instruments, each requiring a separate computer, with the attendant complication of trying to integrate all their signals, makes such multi-sampling economically and technically unattractive.

'Computer' used throughout the description of this invention refers to any device capable of receiving signals from light detectors, and performing the required data reduction and analysis on these signals. Hence, 'computer' can refer to any commercially available computer (e.g. such as those sold by IBM, Dell, Apple, etc.), including workstations (e.g. Sun Microsystems), as well as any microprocessor-based device whether commercially available or designed specifically for the data acquisition and analysis functions described herein.

2) In the emerging field of combinatorial chemistry applied to new polymer synthesis, research and development is focused on running dozens of reactions ('reaction' as used herein refers to both chemical reactions involving the making and breaking of covalent bonds, as well as any reaction that a polymer or colloid can have in response to time, interactions with itself or other agents, etc. that do not involve making or breaking covalent bonds; such reactions can include aggregations of polymers, changes in dimensions, hydrodynamic properties, excluded volume interactions, etc.) in parallel in microliter quantities. No light scattering technology currently exists which can make simultaneous, multiple measurements. In its simplest version, SMSLS will be useful in providing immediate information on whether polymer reactions are occurring at all, and what the relative rate constants are for each sample. In the more refined version, where absolute calibration would be made and exact sample concentration known or measured, the device would give absolute molecular weight characterization in real-time of the polymers as they polymerize. Again, such analyses can be made with a single device and a single computer. The analyses might be carried out on samples flowing through the SMSLS device, pipetted into and at rest in the SMSLS device, or samples in cuvettes which can be inserted into the SMSLS device. Hence, the SMSLS invention is expected to have favorable implications for this emerging field, which is being pursued by academic scientists, multi-national corporations, and small, emerging companies.

3) In university, pharmaceutical, industrial and other laboratories, time-dependent processes can be followed, using SMSLS, on many independent samples of varying composition, in order to determine the evolution and stability of solutions; e.g. determination of the shelf-life of a pharmaceutical product, the stability of an organic polymer in different solvents, the enzymatic degradation rates for polymers, or the interaction of small molecules with larger ones, etc. Users can have direct, real-time, graphical and numerical representations on their computer screens of the simultaneous evolution of many samples. Under current art, such measurements require monopolizing an expensive light scattering device and computer for each sample being tested. With an SMSLS device with, say, 250 sub-chambers ('Sub-chamber' as used herein refers to any sort of receptacle which can receive a liquid sample, and has means for introducing light to be scattered, and a means for detecting the scattered light. The sample can be introduced into the chamber by any means, such as flow, pipetting, being held in a separate sample cell which is inserted into the sub-chamber, etc.), all monitored by a single computer, measurements that might take a year of monitoring might be performed in a single day.

4) In Size Exclusion Chromatography (SEC) applications, and other separation/fractionation analyses, the SMSLS invention can be used as a detector for multiple SEC or other separation/fractionation devices. Currently, a costly light scattering detector is needed for each separation device. With this invention only a single SMSLS device would be needed for multiple separation devices. In this case, a separate computer would most likely be used to analyze the detected light from each sub-chamber, since, normally, there is a dedicated computer for each SEC instrument and the other detectors associated with each (e.g. refractive index detector, viscometric detector, ultraviolet/visible detector, etc.).

5) In a setting where high sample characterization throughput of unfractionated polymer batches is desired, the SMSLS invention could be readily adapted to robotic automation, wherein the samples could be automatically and simultaneously prepared, then simultaneously measured by SMSLS.

In summary SMSLS can be of decisive utility in academic and industrial laboratories that deal with, but are not limited to, polymers, resins, adhesives, foodstuffs, pharmaceuticals, water purification agents, pulp, paper and fiber products, coatings, etc.

The present invention involves making a single device with multiple sub-chambers, each of which is equipped with its own independent scattered light detection means (e.g. one or more optical fibers, window(s), etc.). Each sub-chamber can hold an independent liquid sample, and light is incident on each sub-chamber. The scattered light from each sample will be detected by the detection means in each sub-chamber. Each detection means is coupled to its own light sensitive detector (e.g. a photodiode or charge coupled device), the output of which is led into a computer for analysis. Hence, the device permits multiple, independent samples to be measured simultaneously and analyzed by a single computer.

A technical clarification of the meaning 'simultaneous' in the context of SMSLS is in order. In general the analog or digitized voltage values of the photodetectors for each sub-chamber are read sequentially, so that, technically, one sub-chamber value might be read microseconds, milliseconds or seconds before the next one. In this case, 'simultaneous' means that the values from all the individual sub-chambers, or a subset of the sub-chambers, are read (and recorded and/or processed), before another round of data is collected for some or all of the sub-chambers, even when the sub-chamber voltages are read sequentially during a given data collection round. This definition also applies to the case where multiple sequential readings of all sub-chambers are made during a given round in order to average the signal from each chamber.

The sub-chambers can be fabricated all with the same volume, or different volumes can be assigned to the fabrication of individual sub-chambers or groups of sub-chambers. Sub-chambers can be designed and fabricated with a wide variety of volumes. In micro-chemical applications, the sub-chambers will typically have volumes of from 5 microliters to 200 microliters. In situations where sample volume is less critical, sub-chambers can typically have volumes from 200 microliters to 2 milliliters. There may be some contexts, particularly in industrial settings where huge reactor volumes are used (e.g. 1000 gallon reactors), and so small sub-chamber volume is not a critical issue. In such cases sub-chambers may typically hold volumes from 2 milliliters to over 20 milliliters.

The device only needs to have a single incident source of light (e.g. a laser) that irradiates the main chamber containing all of the sub-chambers, although multiple light sources can also be used, as detailed below. This can be achieved in series-mode, or parallel-mode:

In the series-mode, the incident light is collimated and sent through a line of sub-chambers, in series, each separated by a transparent window. There can be more than one light source and sets of sub-chambers.

In the parallel-mode, the light can be split at its output so that each sub-chamber receives its own, independent portion of the incident light, in parallel. Alternatively, each sub-chamber or set of sub-chambers can have its own unsplit light source.

One advantage of the series-mode is that little power is lost from sub-chamber to sub-chamber, and only one light source is needed per line of sub-chambers. The disadvantage is that if a window(s) between sub-chambers fouls (e.g. from a 'dirty' sample), or a sample in a sub-chamber becomes turbid, then all the sub-chambers down-beam will be affected. Series-mode is expected to be of greatest utility when the samples remain transparent and don't become cloudy in time, or otherwise undergo large changes in light transmittance.

In the parallel-mode, there is no problem if any one sub-chamber fouls, but there will be an additional cost due to the beam splitting and/or additional light sources. This mode will be especially valuable when the stability and/or evolution of polymer and/or colloid samples leads to significant turbidity in the samples.

In either series- or parallel-modes, each sub-chamber can be independently filled with sample solutions. This can occur in a number of ways: i) the samples can be introduced into sub-chambers via a pumped flow, ii) they can be pipetted, or otherwise manually or robotically transferred into the sub-chambers, or iii) each sub-chamber can contain its own miniature receptacle for inserting a cell.

In its simplest form, the light scattering can give immediate information about relative polymer and/or colloid size, stability and evolution of samples, and show whether a polymerization reaction is occurring or not. In its more refined version it will allow the absolute mass of polymers and/or colloids, and their dimensions to be determined. It is possible that other spectroscopic devices could be incorporated in the invention, such as dynamic light scattering, ultra-violet absorption, and refractive index. A viscosity detector might also be incorporated when flow is present.

In principle, dozens, hundreds or more such sub-chambers can be incorporated into the device of the preferred embodiment of the present invention. The sub-chambers can be individually stacked together to provide the user with exactly the number needed, or the device can be manufactured with a fixed number of sub-chambers, and the user just utilizes the number necessary. It is also possible to use multiple light sources (e.g. lasers), wherein each light source irradiates a chamber with one or more sub-chambers. In this case, all the data would still be processed simultaneously by a single computer, except in special cases where multiple computers might be desirable (e.g. when output streams from several independent fractionation devices flow through sub-chambers in the device), The cost of the chambers should be quite low, because they can be fabricated out of plastics, such as Delrin, blackened metals, or glass. The separating windows in series mode can be inexpensive borosilicates, such as high quality microscope cover slips, which cost only pennies apiece. Flow fittings, which would be optional, can be made from conventional HPLC plumbing or other commercially available or custom built materials. The optical fibers are also inexpensive. Light sources are also inexpensive; e.g. a diode laser with collimation optics, a diode laser without special optics, integral arrays or banks of diode lasers, light emitting diodes, incandescent, gas or arc lights. Likewise, photodiodes, photomultipliers or other detector types (e.g. diode arrays, charge-coupled devices, etc.) are relatively inexpensive.

It is stressed that individual sub-chambers do not need to be in physical contact with each other (e.g. as shown in FIGS. 4, 8 and 9), especially in parallel-mode, where there is not necessarily any advantage to them being in contact. In many cases, however, close, regular spatial proximity of the sub-chambers will enhance the ease of robotic or manual testing; e.g. pipette devices with multiple tips at fixed distances are readily available (for example, the Multichannel Pipette from Rainin Instrument Company allows simultaneously filling sample cells or sub-chambers at fixed spatial separation).

Definitions of SMSLS

The Following is a Necessary and Sufficient Condition for a Light Scattering Device to be Considered an SMSLS Device.

An SMSLS device is one in which there are always two or more sub-chambers capable of making at least two or more simultaneous measurements on independent samples, even if, at any given time, only one sub-chamber is in use. By this definition there is no SMSLS device with a single scattering chamber that can act as a stand alone device.

Indivisibility: An SMSLS device cannot be taken apart into individual single sample stand alone units (i.e. individual units that could be placed in remote locations and function independently) without the introduction of extra materials (e.g., any one or more of the following; mounting plates, enclosures, fiber optics, lenses, light baffles, light sources, detectors, electrical wires, plumbing connections, baseplates, brackets, electronic circuits, etc.), and/or special procedures such as re-alignment, reconnection of optical, plumbing and electrical connections, etc. Computers and identical software copies are excluded from this definition since they might be needed for completely independent operation of each unit.

Non-constitutibility from stand alone units: An SMSLS unit cannot be constituted from two or more stand alone units without the introduction of an additional, indispensable component(s), whether these be electronic, software, hardware, mechanical, plumbing, etc. Specifically this includes multiplexers, signal processors and/or software with SMSLS capability. In the case of software, this includes software that can store data from independent, simultaneous scattering experiments that could later be analyzed by separate software to yield the results of the independent experiments.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 3 shows a hybrid series/parallel-mode with a single light source.

FIG. 4 shows a bank of light sources (e.g. lasers), each illuminating one or more sub-chambers.

FIG. 5 shows details of a series-mode chamber with individuals cells for insertion into each sub-chamber, and index matching between sub-chambers.

FIG. 6A is a cut-away view, and FIG. 6B is a top view (which is the same as bottom view) of a series-mode chamber with multiple angle detection. A flow fitting for top and bottom is shown for the case where sample is to be pumped through each sub-chamber. The same type of flow fitting will apply to the other chambers.

FIG. 7A shows details of a top view of a series-mode chamber, with single 90 degree light detection means, which can be either mounted photodetectors, or optical fibers that lead the scattered light to a photodetector.

FIG. 7B is a side view of the series-mode chamber of FIG. 7A.

DETAILED DESCRIPTION OF THE INVENTION

Novelty of the Invention

Figure 2:
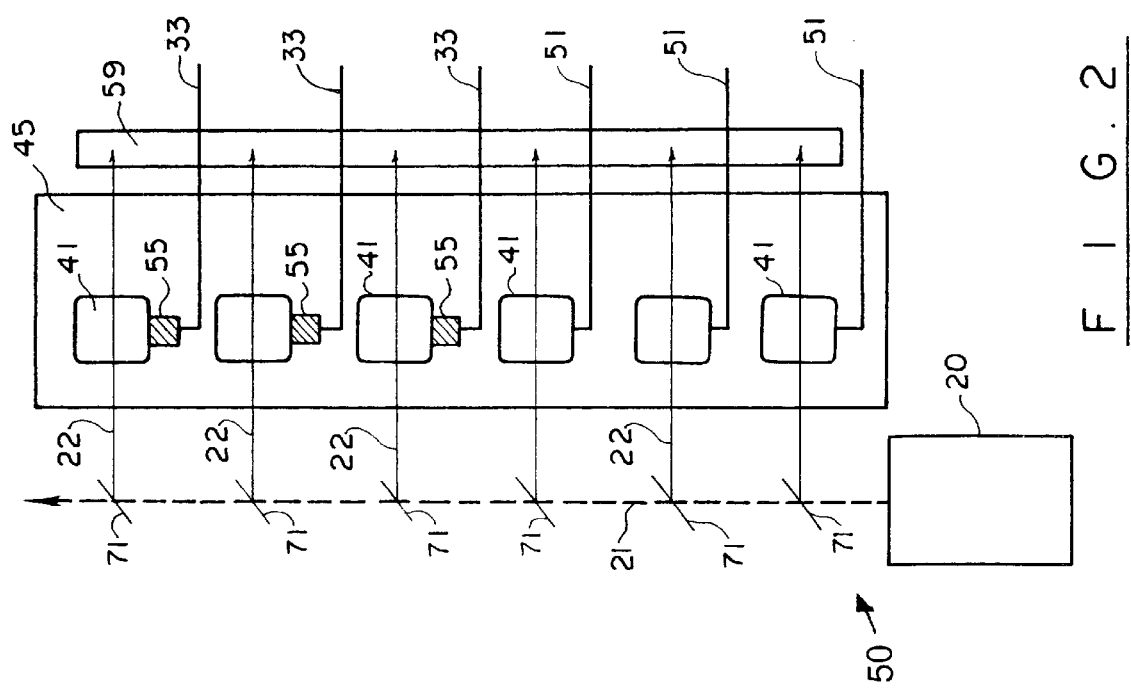
FIG. 2 shows a typical parallel-mode arrangement

The inventor believes SMSLS represents a genuine breakthrough in terms of speed, efficiency, sample throughput, cost and the new applications it makes possible. It must be noted that, to the inventor's knowledge, no unit is commercially available with SMSLS capabilities.

Furthermore, the existing state-of-the-art instruments the inventor is aware of cannot be modified to become SMSLS units, unless they use the idea of the invention presented here, and their systems entirely re-engineered.

Description of the Invention

The invention comprises a plurality of sub-chambers, into each of which a liquid sample can be introduced, either by pipetting or otherwise transferring a small volume (which can be accomplished manually or by a robotic device), flow through couplings and tubing, or contained in insertable sample cells. The liquid sample contains polymer and/or colloid samples, generally in the concentration range of $1 \times 10^{-9}$ to $1.0$ g/cm$^3$, and with molar masses ranging from about 500 g/mole to $10^{12}$ g/mole. In the case of polymerization reactions, monomeric or oligomeric precursors in liquid form might constitute 100% of the sample (i.e. no solvent present), even though these may solidify in the course of a reaction.

The incident light is scattered from the polymers in each sub-chamber, and is detected by independent detectors for each sub-chamber. The incident light source will normally be monochromatic, with a bandwidth of preferably less than several hundred Angstroms, and preferably less than fifty Angstroms. Broad band light sources (e.g. incandescent, arc, fluorescent sources, etc.) with selectable wavelength filters can also be used, to provide a plurality of wavelengths. In some cases it may be desirable to select different incident wavelengths for different sub-chambers or groups of sub-chambers. The light source will preferably be collimated, and a laser provides a convenient means for this. In most of the figures the light source is shown as a laser, for convenience, although other light sources can be used, as just mentioned. The intensity of the incident light will normally be in the range of 0.01 milliwatts to 100 milliwatts, although powers greater or less than these limits might be used in some applications. The central wavelength of the light source will typically be in the range of 200 nanometers to 1,400 nanometers.

In some versions of an SMSLS device it will be advantageous to employ commercially available arrays of diode lasers for parallel or hybrid series/parallel operation; e.g. an ATC-Q25-5 25 W laser diode array from DLK Lasers, France. The availability of diode laser arrays with different properties is a rapidly growing area, so it is expected such devices will play a prominent role in the continuing development of SMSLS devices.

Polychromatic light can also be used in cases where qualitative changes in light scattering due to instability, aggregation, microcrystallization, etc. are to be monitored.

A given light source can be used to provide an incident beam for one or more sub-chambers. In some designs it may be desirable to have one light source (e.g. laser) for each sub-chamber.

The plurality of photodetector signals from all the sub-chambers can then be led into a computer for simultaneous analysis. Alternately, photodetector signals can be routed, individually or in sub-groups, to separate computers. The types of computer analyses made on the signals can include, but are not limited to:

1) Relative changes in intensity that indicate if such processes as polymerization, degradation, aggregation, crystallization, phase separation, dissolution etc. are occurring.

2) Absolute determinations of equilibrium values of polymer weight average molecular weight $M_w$, and sometimes z-average mean square radius of gyration $<S^2>_z$ (if the polymer dimensions are at least 1/100 of the incident light's wavelength) or other conformational and/or size information, and sometimes information on interactions, such as the second viral coefficient $A_2$ (e.g. as described by B. H. Zimm, "The Scattering of Light and the Radial Distribution Function of High Polymer Solutions", J. Chem. Phys., 16, 12, 1093–1099, 1948). Determinations of these quantities from the absolute value of light scattered by a liquid containing polymers or colloids, usually obtained by relating the relative scattering to that of a well known standard (e.g. toluene), is a routine and well-established procedure.

3) Absolute determinations of the characteristics in 2) when non-equilibrium processes are occurring, such as those mentioned in 1). Additionally, kinetic rate constants and mechanistic information can be obtained from monitoring the non-equilibrium processes.

4) Absolute determinations of equilibrium values of the characteristics in 2) when the polymer is fractionated by some means, such as Size Exclusion Chromatography, Hydrodynamic Capillary Fractionation, Flow Field Fractionation, etc.

5) Large changes in relative intensity, that may occur gradually or abruptly, and which may signal important physical processes such as solution instability, aggregation, strong interaction of co-existing species, precipitation, etc.

The speed of modern microcomputers easily permits the data to be gathered, analyzed and displayed on the screen in an online fashion, so that continuous monitoring, whether by a person, robot, or feedback control automation system can easily be achieved. Naturally, all the data are stored so that extensive post-experimental analysis can also be performed.

Typical sampling rates for each individual sub-chamber may range from milliseconds for fast processes, or when large particle discrimination via scattering spike recognition is used, to tens of seconds, or even longer, for very slow processes, such as shelf-life stability monitoring.

Figure 1:
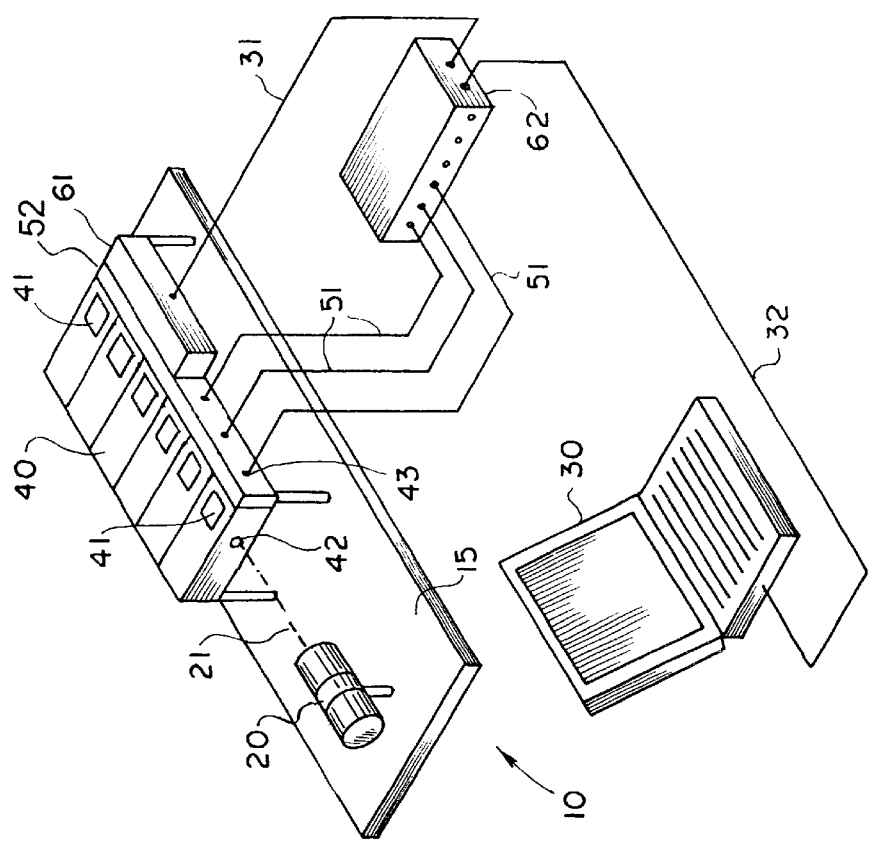
FIG. 1 shows a typical series-mode arrangement.

FIG. 1 shows a typical SMSLS device 10 in series-mode. Endplates (not shown) are optional, and provide input and output windows for the chamber, with a beam dump on the output side. A chamber 40 having blocks including sub-chambers 41 is shown, and two similar blocks not including such sub-chambers 41 could also constitute endplates. The number of sub-chambers is at least two, but has no fundamental upper limit on the number. For example, the last column in table I indicates that hundreds, even thousands of chambers could be placed in series with a substantial fraction of the light surviving to the last chambers in series. The detector plate 52 can be removable, or be made as an integral part of the chamber, and holds the detection means. It also contains the apertures 43 that define the scattering volume of solution viewed by the detectors. The detectors can be any type of directly mounted array of photodetectors 61, or optical fibers 51, that lead to a photodetector array 62.

The photodetector array 61 can consist of a wide variety of designs. For example, the scattering output signal from each sub-chamber 41 can be incident on an individual photodiode. A Charge Coupled Device (CCD), although an integral unit, reads light intensities via a plurality of contiguous, light sensitive pixels. Hence, it is possible to have the output light from each independent sub-chamber 41 fall on one or more pixels within the CCD array, and individually read the pixels corresponding to that sub-chamber 41. Thus, a single CCD can actually constitute a means of independently monitoring the scattered light levels in an SMSLS device 10.

FIG. 2 shows a typical SMSLS device 50 in parallel-mode. The sub-chambers 41 receive incident light beams 22 that are split off from the principal beam 21 by beam splitters 71. There is an optional beam dump for each sub-chamber 41, optionally incorporated into a beam dumping plate 59 which can be optionally removable. Individual photodetectors 55, can be mounted next each sub-chamber 41, the wall of which contains an aperture for defining the scattering volume of each detector, or optical fibers 51 can be in their place, and their signals led to a photodetection bank, such as array 62.

FIG. 3 shows a hybrid series/parallel device 60, wherein a collimated light source (e.g. laser 20) is used. The beam 21 is split into sub-beams 22, as in the parallel-mode of FIG. 2, and each sub-beam 22 enters a group of sub-chambers 41 in series. The number of sub-chambers 41 in each series is arbitrary, and does not need to be equal from sub-beam 22 to sub-beam 22. Again, any combination of fixed photodetectors 55, optical fibers 51, or other detection means can be used.

FIG. 4 shows a hybrid system 70 containing several different arrangements of series-mode, parallel-mode and combined series/parallel-mode sub-chambers 41. One or more sources of light can be used. Any combination of parallel-mode and series-mode is possible, such as combining one or more chambers containing sub-chambers in both parallel-mode and series-modes. The entire instrument 70 can all be housed in a single, small enclosure, and the photodetector outputs from all sub-chambers 41 can be fed into a single computer, or a plurality of computers. FIG. 4 also shows examples where several of the sub-chambers 41 are not in physical contact with each other. Photodetecting means are not shown in FIG. 4, but can be the same as in FIG. 3.

FIG. 5 shows an SMSLS device 80 including an insertion chamber 90. In this, there are contiguous sample cell holders 91, or wells, which may be in a single piece, or in separate pieces. Sample cells 92 containing individual samples are inserted into the cell holders 91. Detection can follow any of the previously listed modes. A further feature of contiguous insertion wells, which communicate with each other such that liquid poured in the chamber reaches each well, is that an index matching fluid (e.g. water, toluene, etc.) can be introduced. Hence, when a sample cell 92 is inserted, the index matching fluid surrounding the cell greatly decreases incident beam reflection losses from cell to cell and also reduces stray light. Such index matching is commonly used in single sample light scattering. Sub-chambers are shown as circular in FIG. 5, but can have any shape; e.g. rectangular.

FIGS. 6A and 6B show a multi-angle SMSLS device 100 including a multi-angle SMSLS chamber 93. In this, three different scattering angles are monitored per sub-chamber 94. In principle, there is no limit to the number of scattering angles which can be used per sub-chamber 94, although practically two to fifty angles should be adequate. Shown in FIG. 6B is a flow fitting assembly, which is on the top and bottom of the chamber 93, which includes fittings 95. This allows many samples to be independently pumped through the individual chambers 94. This same type of flow assembly can also be used in parallel-mode and hybrid-modes, as well as in any of the single angle devices described above.

Whereas many inexpensive commercial lasers are available with high output stability, use of less stable sources, e.g. incandescent sources or unstabilized lasers, might require that a portion of the incident beam be split off for continuous monitoring of intensity, which would serve to correct for any intensity variations. This technique is often standard, especially in older instruments which have less stable light sources.

The chambers can be hollow cavities in opaque plastic, for example, with appropriate windows provided to allow a light beam to enter the chambers and light detecting means to optically communicate with the chambers.

In the array shown in FIG. 4, the light detection means are not shown. All light detection means from all sub-chambers in FIG. 4 can be fed to a single computer for analysis, or they could be fed to separate computers.

Though typically lasers are shown in the drawings, other appropriate light sources could be used.

In general, the number of chambers shown in the drawings is arbitrary; certain applications may dictate the appropriate or ideal number of chambers for a particular project.

Each chamber or subchamber may have a single light detecting means or multiple light detecting means.

In constructing the subchambers not only is the total sample volume of each subchamber important, but also the scattering volume of each. The scattering volume is defined as the portion of irradiated volume of sample that a given photodetector receives light from. In the designs contemplated here, the scattering volume may typically range from less than 1 nanoliter to over a microliter; i.e. the scattering volume can be several orders of magnitude smaller than the sample volume.

The scattering volume is determined by the irradiating beam profile, and the segment of it received by a detector. For a collimated laser beam the scattering volume is basically the beam cross-sectional area times the length of beam detected by whatever apertures, optical fibers, windows, etc. define the acceptance to the detector. Focusing a laser beam provides a way of obtaining very small scattering volumes, since focusing produces a spot, whose diffraction limited waist is defined by the wavelength of the light, the lens focal length, and the diameter of the unfocused beam. Typically, scattering volumes from less than 1 nanoliter to 50 nanoliters can be achieved with focused beams and fiber optic detectors. The largest single advantage of a small scattering volume is that it is less susceptible to large bursts of scattered light caused by stray particles in a liquid scattering sample. In fact, the fraction of detection time free from particle bursts decreases exponentially with increasing scattering volume.

Small scattering volume hence places less stringent requirements on how free a sample must be of stray particulates in order to make useful measurements. It also allows the number density of such particles to be determined simultaneously with the characterization of co-existing polymers or colloids. In some cases, large particles are not merely impurities, but integral to a sample; e.g. bacteria or yeast that produce polysaccharides or proteins, or that degrade them via fermentation, microgels or crystallites that may form in a polymerization reaction, aggregates of proteins that might form from product instability, etc. The method of Schimanowski et al. for this is described in ref. 10 herein (R. Schimanowski, R. Strelitzki, D. Mullin and W. F. Reed, "Heterogeneous Time Dependent Static Light Scattering", Macromolecules, 32, 21, pp 7055–7063, 1999)

In general, focusing of incident light to provide a small scattering volume will be most easily accomplished in the parallel mode, where each subchamber receives its own beam. Although the means of detection of scattered light can be accomplished by various means, one of the best is to use, for each detection angle, an optical fiber inserted through the sub-chamber wall to be either flush or slightly recessed from the inner sub-chamber wall. When flush, the acceptance of scattered light by the fiber is defined by the fiber's numerical aperture. When recessed, the acceptance is defined by the 'pinhole' in which the fiber is recessed. If the fiber is recessed too far, however, an air pocket can form between the inner chamber wall and the end of the fiber in the recessed hole, leading to loss of light detection.

Details of a Particular Embodiment of a Series-mode SMSLS Chamber

Figure 7C:
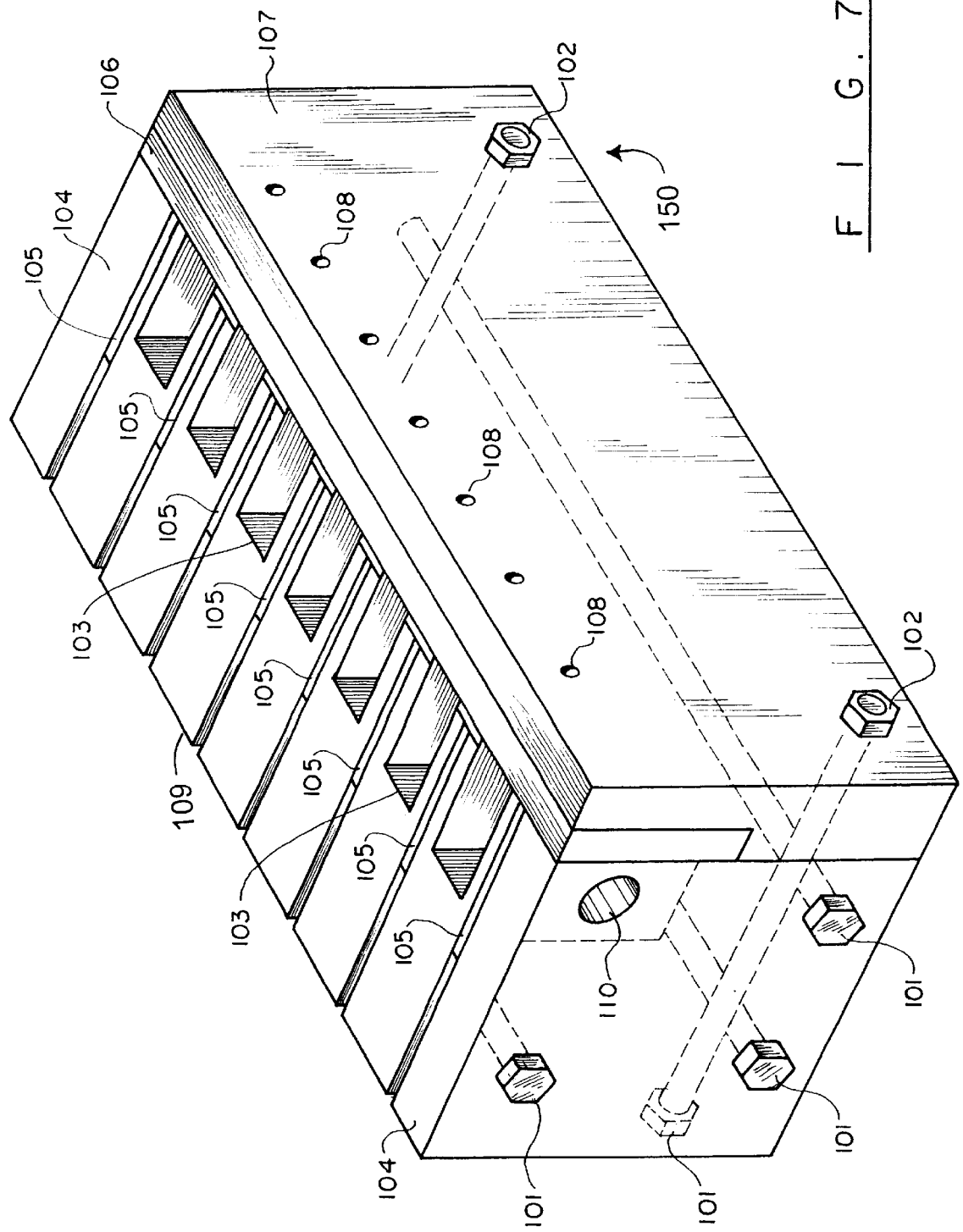
FIG. 7C is a perspective view of the series-mode chamber of FIG. 7A.

FIGS. 7A, 7B, and 7C show details for a particular series-mode chamber 150 with a single detection angle at 90 degrees (i.e. perpendicular to the incident beam 21). This is not to be taken as the sole type of embodiment of the device, but provides a practical scheme, which solves some of the design aspects. The body 109 is made out of a preferably rectangular piece of dark, preferably black, material. This can be a black plastic, such as Delrin, anodized aluminum, or blackened glass. Rectangular, circular or elliptical sub-chambers 103 are made in the plastic (e.g. by milling or boring). A hole 110 goes through all the sub-chambers 103 for the incident light beam 21 to pass through. Various means of separating the sub-chambers 103 can now be used. One is to fix, by cementing, pressing or ring-retaining cylindrical windows between the sub-chambers. Shown in FIGS. 7A–7C is a different method that consists of making holes for securing cross-bolts 101 longitudinally and laterally into the chamber body 109, then sawing through the chamber 150 completely, inserting between each pair of sub-chambers 103 a flat window, such as a microscope slide 105, which is rimmed with thin Teflon or other gasket material. The chamber 150 is then re-assembled with longitudinal through-bolts 101 whose holes were made before the chamber 150 was sawed apart. Re-assembly with the through-bolts 101 assures compression of the gasket material on the sub-chamber separating windows 105, and hence leak-proofs the sub-chambers 103. Optionally, a longitudinal, external clamping plate can also be secured to the ends of the chamber on the upper, outer edge of the sub-chamber side, to insure additional compression of the gaskets.

The scattered light must now be detected. If the sub-chambers were made with walls of the chamber material on all four sides, then windows can be secured in each sub-chamber by providing a hole in the wall closest to the edge of the chamber. Such windows can be cemented in, ring-retained, held by chucks, or otherwise retained. They might also consist of optical fibers secured in the wall. An appropriate aperture can be made external to the window, or by a fiber itself to define the scattering volume measured by each photodetector. Another means of achieving detection is to have the sub-chambers 103 milled or cut into the chamber body 109, as in FIGS. 7A–C, such that the outer wall is open. A long, transparent sheet of material, such as a microscope slide 106, can then be rimmed with gasket material around the edges and between the sub-chambers 103, and then be sandwiched and pressed between the open sub-chamber side of the chamber and an aperture/detector plate 107. The holes that were cut laterally in the chamber before sawing the sub-chambers apart are used to secure and squeeze the transparent sheet 106 between the chamber body 109 and the aperture/detector plate 107. The aperture plate 107 has apertures 108 that define the scattering volume of the attached photodetectors (not shown in FIGS. 7A–C), or be used to secure optical fibers in place, or otherwise be used to form the scattering volume and provide for scattered light detection.

The chamber 150 thus constructed can then be filled with independent samples, one in each sub-chamber 103, and a collimated light beam 21 (FIG. 7B) can then shine through the hole 110 initially made longitudinally in the chamber body 109 between sub-chambers 103 for this purpose. The scattered light is then photodetected, fed into a computer(s), and analyzed as described above.

It is also possible to make a flow version of this cell by providing inlet and outlet flow fittings on the top and bottom of each sub-chamber. In the particular version shown in FIGS. 7A–7C, flow fitting holes could be simply made in the bottom of each sub-chamber 103 and tubing attachment bores and couplings made on the exterior of the bottom, and a flow fitting assembly with holes, tubing and couplings could be attached as a plate to the top of the entire chamber.

Typical dimensions of the sub-chambers are quite arbitrary. A typical example might be where the sub-chambers are 3 mm deep, 2 mm long and 4 mm wide, yielding a sample volume of 24 microliters. A typical SMSLS chamber of this design with 20 sub-chambers will have dimensions roughly 10 mm wide, 10 mm deep, and 30 mm long. These dimensions can be adjusted upwards or downwards, as particular design considerations require.

In purely parallel mode the problem of providing liquid-tight light paths between sub-chambers in series is avoided entirely, since each sub-chamber receives its own light beam or portion of a beam. Thus, parallel mode is expected to become an increasingly attractive alternative to series mode, especially since diode lasers and diode laser arrays are becoming increasingly less expensive.

Considerations of Light Beam Intensity Losses for Series-mode:

The series-mode requires that beam power losses from sub-chamber to sub-chamber be considered. These losses will arise from two mechanisms:

1) Reflection losses. These occur at the window as the light passes from one sub-chamber to the next. The ratio of the intensity of the light entering the Nth chamber to the intensity incident on the exit glass-solvent interface $I_I$ of the first sub-chamber is given by $$\frac{I_N}{I_I} = \prod_{i=2}^{N} (1 - \alpha_{i-1})(1 - \alpha_i) \qquad (1)$$

where $\alpha^{i-1}$ is the fractional reflection loss in the $(i-1)^{th}$ sub-chamber, given by (dropping the subscript for clarity)

$$\alpha = \left| \frac{(n_s - n_g)^2}{(n_s + n_g)^2} \right| \qquad (2)$$

where $n_s$ is the index of refraction of the solvent in the sub-chamber, and $n_g$ is the index of refraction of the transparent divider between the sub-chambers. Normally, the transparent divider between sub-chambers will be the same for all (although situations might arise where they would preferably be different; e.g. having different coatings), and the index of refraction will often be the same. In this case $\alpha$ is identical for all sub-chambers, and the fractional intensity of light entering the $N^{th}$ chamber is given by $$\frac{I_N}{I_I} = (1 - \alpha)^{2(N-1)} \qquad (3)$$

For multiple chambers, there can be quite a difference in reflection losses, depending on the index of refraction of the solvent and the divider. Table I shows how the fractional light reaching the $N^{th}$ chamber varies with the composition of the divider and solvent, for three different cases. For all cases the divider is taken to have a typical value for index of refraction of a glass, $n_g=1.5$. The first column is the case where the cells are empty, so that $n_s=1$. It is seen that over half the light incident on the first sub-chamber has been lost to reflection by the time the $11^{th}$ sub-chamber is reached. This case is shown just to illustrate how much light would be lost in empty cells, not during actual measurements where a liquid sample is always present. The second columns takes the solvent as water, with $n_s=1.33$. In this case, only 7% of the light is lost to reflection by the $11^{th}$ sub-chamber, and is reduced below one half after around 100 sub-chambers. The third column shows the case of a typical organic solvent with $n_s=1.45$. Less than 1% of the light is lost to reflection by the $11^{th}$ sub-chamber, and little more than 5% is lost by the $101^{st}$ chamber.

TABLE I

Reflection losses for an SMSLS chamber where each cell is separated by a common, transparent partition of $n_g = 1.5$.

| Chamber N | Fractional light incident when $n_s = 1$ | Fractional light incident when $n_s = 1.33$ | Fractional light incident when $n_s = 1.45$ |
|---|---|---|---|
| 5 | 0.720 | 0.971 | 0.994 |
| 11 | 0.440 | 0.93 | 0.989 |
| 21 | 0.195 | 0.865 | 0.998 |
| 101 | 0.000284 | 0.485 | 0.944 |

For the special case where a transparent cell is inserted into each sub-chamber, there is an additional loss term, because there are now four interfaces between each sub-chamber. The fraction of the light incident at the exit face of the first sub-chamber which is incident on the $N^{th}$ sub-chamber is then $$\frac{I_N}{I_I} = \prod_{i=2}^{N} (1-\alpha_{gb})^2 (1-\alpha_{sg,i-1})(1-\alpha_{sg,i}) \quad (4)$$

where $n_b$ is the index of refraction of the medium between the transparent cells inserted into the sub-chambers, and $\alpha_{gb}$ is the loss factor, computed by eq. 2, with $n_b$ substituting $n_s$. For the case where there is the same solvent in each sub-chamber, the inter-sub-chamber space has the same index $n_b$, And the transparent cells inserted into each sub-chamber have the same index $n_g$, eq. 4 reduces to $$\frac{I_N}{I_I} = [(1-\alpha_{sg})(1-\alpha_{gb})]^{2(N-1)} \quad (5)$$

If the medium between the sub-chamber is air ($n_b=1$), the loss term becomes especially large. The first column of Table II shows the loss figures when transparent cells containing liquid sample of $n_s=1.33$ are inserted into sub-chambers which are separated by air. The large losses, suggest that index matching between sub-chambers might be desirable in such an embodiment; e.g. the sub-chambers would be bathed in an index matching liquid, such as water. The next column shows the losses when the medium between the transparent cells in the sub-chambers is water. The losses decrease markedly.

TABLE II

Reflection losses for an SMSLS chamber using insertable, transparent cells in each sub-chamber, with and without index matching between sub-chambers, when the solvent in each cell has $n_s = 1.33$, and the cells have $n_g = 1.5$

| Chamber N | Incident light, no index matching; i.e. $n_b = 1$ | Incident light, with index matching with water; i.e. $n_b = 1.33$ |
|---|---|---|
| 5 | 0.701 | 0.943 |
| 11 | 0.406 | 0.865 |
| 21 | 0.165 | 0.749 |
| 101 | 0.000123 | 0.236 |

(It is noted in the above computations that $I_I$, the light intensity incident on the exit face of the first sub-chamber, is $I_I=(1-\alpha_{ag})(1-\alpha_{gs})I_o$, where $I_o$ is the intensity of the incident beam in air, and $\alpha_{ag}$ represents the reflection loss at the entrance to the first chamber. Typically $I_I \sim 0.96 I_o$).

The preferred embodiment already includes partial index matching between sub-chambers, by virtue of the fact that the liquid samples in two adjacent sub-chambers share the same dividing window.

2) Scattering losses. These occur as the light passes through the liquid in each sub-chamber. This can be broken down into two effects.

i) The scattering Losses When the Sub-chamber Contains a Typical, Dilute Polymeric or Colloidal Solution.

The Rayleigh ratio, $I_R$ for vertically polarized incident light is simply related to the scattering extinction coefficient (or turbidity $\tau$), via integration over all $4\pi$ steradians of solid angle in a sphere by $$\tau = 4\pi/3 I_R \quad (6)$$

The decrease in intensity for light (e.g. of a laser beam) propagating in the z-direction through a medium of turbidity $\tau$, is $$I(z) = I_o e^{-\tau z} \quad (7)$$

Eqs. 6 and 7 allow an estimation of typical scattering losses that will take place as the beam propagates through a series-mode SMSLS chamber. A typical light source for an SMSLS system would be a diode laser operating at 677 nm. For pure toluene at 25C, for vertically polarized incident light of 677 nm, $I_R=1.07 \times 10^{-5}$ cm$^{-5}$. This value is also quite typical of the type of dilute polymer solutions used in absolute macromolecular characterization by light scattering. To be conservative, ten times this value can be used in estimating scattering losses. By eq. 6, $\tau \sim 5 \times 10^{-4}$ cm$^{-1}$. This means that the incident beam intensity will drop to 37% of its initial intensity after traversing 2,000 cm of typical dilute polymer solution; in other words, the losses in intensity due to scattering in a typical situation are completely negligible. In fact, if 100 sub-chambers were used, each with a 0.2 cm path length, the total scattering loss after passing through all 100 sub-chambers would only amount to 1.5%.

Hence, beam intensity losses for normal, dilute polymer and colloid solutions will in general be negligible. Even in the case where molecular weights are changing in time, and at different rates among sub-chambers, the sub-chamber to sub-chamber fluctuation should be likewise negligible. For example, at a fixed concentration, if a polymer mass changed one-hundred fold, starting at a scattering level equivalent to pure toluene, the decrease in intensity in passing from one 0.3 cm pathlength sub-chamber to the next would be only 0.00000107%. There would hence also be no measurable fluctuations in laser power from sub-chamber to sub-chamber when individual sample scattering varied in Rayleigh ratio at such an order of magnitude.

ii) Scattering Losses When the Sub-chambers Contain Solutions with Large Scattering Particles.

The principle of absolute macromolecular characterization by light scattering is based on the assumption that a detected, scattered photon has scattered only once while traversing a sample solution, and that the individual particles are small enough that they don't individually scatter strongly. The types of solutions typically characterized by light scattering are clear to the eye.

When solutions contain significant populations of large particles, such as aggregates of polymers, polymer/colloid complexes, bacteria, etc. the turbidity τ can be so high that the solution is cloudy. This can be due to either massive scattering (usually treated as Mie scatterers) from individual particles within the single scattering criterion, or multiple scattering from large particles.

Since the SMSLS technique will be used primarily in the case of clear solutions, scattering losses from these mechanisms will not normally come into play.

There are, however, foreseeable uses of SMSLS where cloudy solutions will occur. For example, in monitoring the stability of polymer solutions and/or colloid solutions, e.g. in the pharmaceutical sector, or when testing for the interaction between polymers, colloids and small molecules, solutions may become gradually or suddenly cloudy. Even though absolute macromolecular characterization is no longer possible, the onset and pattern of the strong scattering can itself be a very useful diagnostic for many applications. If cloudiness occurs, however, the beam intensity losses can become significant over the length of the SMSLS chamber, which would compromise the reliability of measurements made down-beam from sub-chambers containing cloudy liquids. In such cases, the parallel-mode SMSLS chamber would be a preferable alternative. Since each sub-chamber can be completely independent in the parallel-mode version, none of the foregoing intensity loss considerations would be important any longer.

Incident Intensity Losses in Parallel-mode, Per Light Source.

As mentioned, parallel-mode has the advantage of making each sub-chamber optically independent of all other sub-chambers. The disadvantage is that the light intensity entering each chamber will be reduced in proportion to the number of parallel sub-chambers used per light source. As mentioned, however, this concern is likely to diminish since laser diodes and diode laser arrays are becoming inexpensive. The following illustrates the types of intensity losses to be expected per each group of sub-chambers irradiated by an independent source, whose output is split for incidence on its corresponding group of sub-chambers.

The parallel-mode normally involves using some sort of beam splitter for each sub-chamber. If the initial intensity of the beam is $I_o$, and the reflectivity of the beam splitter for chamber i is designated $R_i$, then the intensity incident on chamber i is given by $$I_i = \prod_{j=1}^{i-1} (1 - R_j) R_i \quad (8)$$

If all reflectivities are the same, R, then $$I_i = R(1-R)^{i-1} \quad (9)$$

For example, with R=0.05 and twenty chambers, the first chamber will have an incident intensity of $0.05I_o$, whereas the twentieth will have $0.018I_o$.

A simple and inexpensive beam splitter could be a microscope cover slide. It is conceivable that if a specific gradation of intensities were desired, including keeping the intensity incident on each sub-chamber approximately constant, then beam splitters with special coatings could be used, so that different values of R would be produced.

It is not necessary, in any of the series-, parallel- or hybrid-modes, for the intensity of the incident light on each sub-chamber to be equal, nor even necessarily comparable. This is because, in the case where relative scattering intensity changes are monitored, such changes in a given sub-chamber are related only to scattering values within that given sub-chamber. In the case where absolute scattering values are necessary or desired, these will be obtained by introducing a reference solution (e.g. toluene) into each sub-chamber and measuring the scattering in each sub-chamber.; i.e. in either the relative or absolute case, the scattering measurements are self-contained and self-consistent in each sub-chamber.

In some SMSLS devices where there is a separate beam, or portion of a beam, for each sub-chamber then there will be no concern about beam intensity losses at all.

Examples of Alternate Parallel-mode SMSLS Systems

Although lasers with collimated and/or focused outputs will often be the preferred light source for SMSLS, other light sources and configurations are possible, and this invention is meant to include other such scenarios.

Figure 8:
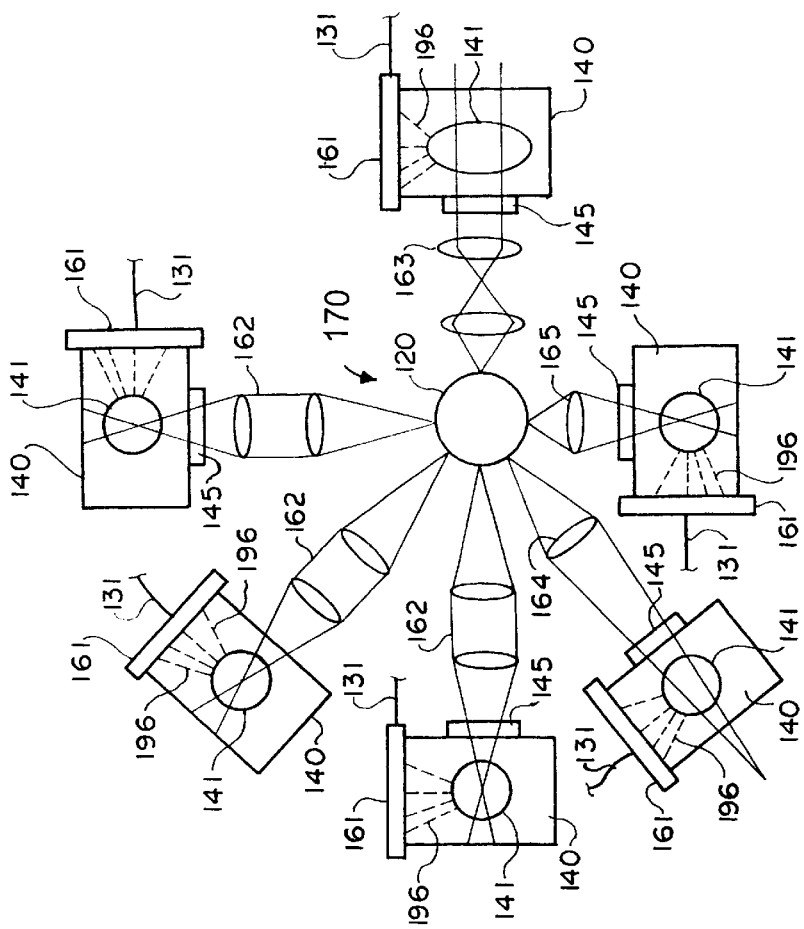
FIG. 8 shows a scheme with an isotropic light source which is used as an alternate means of producing parallel-mode. An ordinary incandescent source with suitable wavelength selecting filters for each sub-chamber is used.

1) One example is given in FIG. 8, wherein a SMSLS system 170 includes sub-chambers 141 are stationed around a simple, non-collimated, polychromatic light source 120 (e.g. a gas discharge, arc lamp or incandescent bulb). The light from the source can then be collimated, focused or partially focused independently to pass through each sub-chamber. Collimation, focusing and partial focusing are achieved by using standard arrangements of lenses, apertures and pinholes, as are commercially available (e.g. Edmund Scientific, Rolyn Optics, Newport, Melles-Griot, etc.). Shown in FIG. 8 are focusing lens assemblies 162, 165, a partially focusing lens assembly 164, and a collimating lens assembly 163. Light detector arrays 161 detect light traveling through passageways 196 in blocks 140. This arrangement is still formally a parallel-mode SMSLS system, as defined herein, because each sub-chamber 141 receives its own, independent incident light, and will not be affected by fouling or failure of other sub-chambers 141. If a broad-band light source is used it can either be filtered in its entirety (e.g. by an enclosure which is itself a wavelength band-pass filter), or, optionally, wavelength bandpass filters 145 can be placed before one or more sub-chambers 141. In this latter case, it might be advantageous to use different wavelengths for different samples (e.g. some samples have smaller polymers and colloids than other samples; shorter wavelength light could furnish size information on the smaller particles that longer wavelength light can not).

Figure 9:
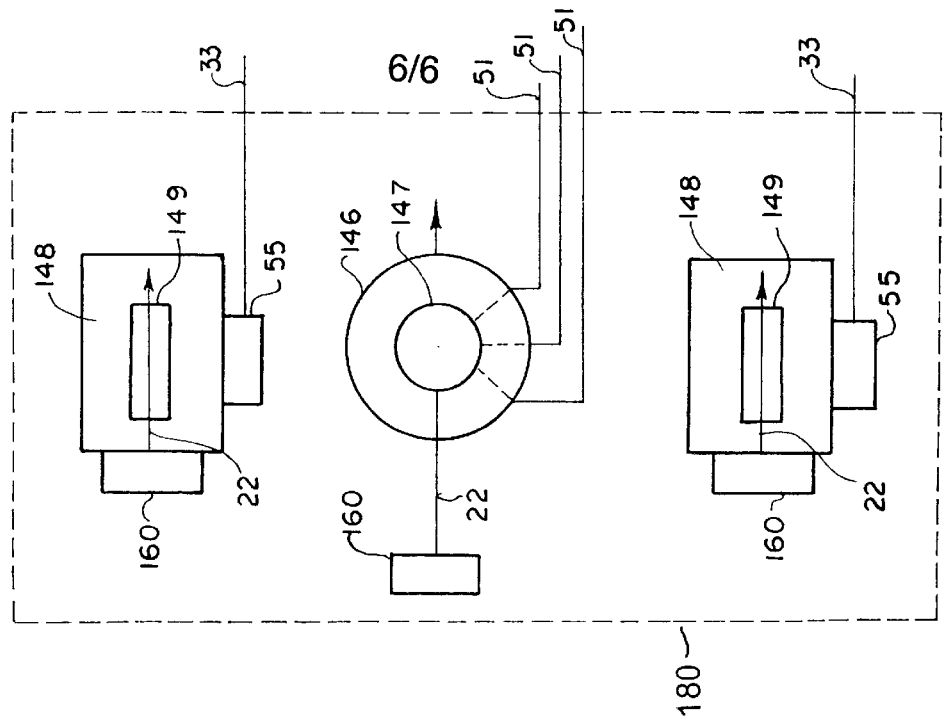
FIG. 9 shows a parallel-mode system in which each sub-chamber has its own light source; e.g. a photo-diode, normally, although not necessarily with a collimating lens, a diode laser with or without additional collimating or focusing optics, light bulbs, etc.

2) FIG. 9 shows a parallel-mode system 180 in which each sub-chamber 147, 149 has its own light source 160; e.g. a photo-diode, normally, although not necessarily with a collimating lens, a diode laser with or without additional collimating or focusing optics, light bulbs, etc. The light source 160 is shown as in contact with blocks 148 containing sub-chambers 149, and spaced from block 146 containing sub-chamber 147, though physical contact with the blocks is optional in any event.

Examples of SMSLS Applications
1. Large Scale Parallel Testing of Solution Stability.

A manufacturer has created a solution containing polymers, colloids, and perhaps many other complex additives. This might be a pharmaceutical solution (e.g. insulin), a material used for coatings (e.g. fluoropolymers), a mixture of syrups and gelatin for the confectionary industry, or many other types of multicomponent solutions. The solution is originally optically clear and scatters relatively little light. In time, however, the solution may become unstable and lose its desired properties. Over a long enough period of observation the instability might manifest itself as a cloudy (turbid) or precipitating solution, or there may be no obvious change in turbidity. Light scattering, by its fundamentally strong dependence on the mass of microscopic particles, is exquisitely sensitive to even slight changes in solution stability. Whether microscopic components of the system begin to aggregate to form dimers, trimers, microgels, microcrystals, crosslinked entities, micro-organized structures, etc. such processes will be detected as soon as they begin; i.e. while the solution is still in the single scattering regime, and long before they become detectable by turbidity or the naked eye. Such aggregation processes can take seconds, hours, days, months or even longer.

An industry seeking to optimize the stability of such products cannot afford to tie up an expensive light scattering instrument for long periods to observe single samples. Simple visual or turbidometric observations are often too insensitive and non-qualitative to be of any use or interest. With an SMSLS device the situation is radically different. Hundreds or even thousands of chambers in the SMSLS device can each accept an independent sample, or formulation, whose stability is to be tested. The liquid samples can be introduced by humans or robots into sub-chambers, or small cells containing the different sample solutions can be inserted into the sub-chambers. There may even be cases where it is most advantageous to flow samples through the SMSLS chambers in a continuous fashion with a pumping device. No matter how the samples are introduced, the light scattering from each sample in its chamber is independently and continuously monitored by an optical detector(s), and the signals from all the chambers are monitored by a single computer (several computers could also be used, if desired). The intensity from each cell could be treated as a relative value, or converted to a relative or absolute average mass by standard light scattering methods. The data representing each sample can be displayed on a computer screen in any number of ways; relative values of samples could be superposed as a function of time so that any evolution in scattering intensity, and hence solution stability, can be seen at a glance. Function keys or 'mouse clicks' can be used to blow up time scales, focus on subgroups of cells, give both numerical and graphical representations, etc. There could also be programmed scattering thresholds that would immediately indicate on the computer screen which samples had reached their instability threshold, etc. In short, detailed records of each sample over arbitrarily long periods of time could be gathered, stored and processed in realtime in any way desired.

Depending on the needs of the industry, each chamber could be subjected to its own environmental factors. It is possible to control the temperature of individual sample chambers or subsets of chambers to see how temperature affects the onset of instability. Other cells might be subjected to visible or ultraviolet light or other radiant energy to determine stability.

The same scenario as above could be used to test the stability of products in the sense of degradation and breakdown. An industry might want to test the stability of a polymer against agents such as enzymes, heat, radiation, acids, bases, microbes or other agents. In this case the breakdown of the polymers leads to a decrease in the scattering of light, so that stability in terms of polymer breakdown can also be monitored. Although such stability tests might be largely empirical in their interpretation (e.g. the scattering intensity of the solution in chamber #x fell by 50% after being exposed 2 days to a certain intensity of ultraviolet radiation), there has been published activity in quantitatively relating light scattering time dependences to polymer structure and modes of degradation.[2,3,4,5] Potential uses for the degradation monitoring could include processing of industrial polysaccharides such as pectins, xanthan, carageenan, alginates, galactomannans, etc., microbial fermentation of natural polymers, biodegradability of synthetic polymers and biopolymers, resistance to heat, light, etc. of polymers used in coatings, adhesives, etc.

In all the above scenarios the experimenters would, by virtue of the data recorded, have quantitative kinetics of any instability processes. Thus, not only are the kinetics of measured samples determined, but modeling and predictions based on these can guide further product development and testing. Techniques from combinatorial chemistry can also be applied.

2. High Throughput Screening in Polymer Synthesis

Many advances in current polymer science depend on the development and testing of novel monomers, catalysts, initiators, chain transfer agents, comonomer types and ratios, reaction pathways and conditions, etc. In many instances there are so many agents and process parameters to test that the only economically viable solution is to carry out many reactions independently, but in parallel. SMSLS promises to contribute immediately to this area by being able to simultaneously monitor many independent reactions.

There are too many situations for solution polymerization to cover all of them here. In some cases it might be desirable to merely know whether polymerization is occurring at all and, if so, at what approximate rate. In this case micro-batch polymerization can be carried out in the many chambers, which might be outfitted for maintaining low pressure, inert atmospheres, etc., and the relative increase in scattering intensity will indicate whether polymerization is occurring and what the time dependence is. If the polymerization is of the step-growth type then relative or absolute weight average polymer masses can be computed directly from the scattering, using standard techniques, as long as the starting concentration is known. In the case of chain-growth reactions, however, the concentration of polymer must be separated from that of monomer in order to obtain relative or absolute masses. A means for doing this online has been recently published (Florenzano, Strelitzki and Reed, ref. 1). Further possibilities include determination of reactivity ratios of comonomers in copolymer reactions, grafting kinetics, and dendrite growth rates.

In the case where absolute mass and kinetics can only be obtained by having a sufficiently dilute, solution it is possible that the automatic, continuous dilution technique (detailed in my pending U.S. patent application Ser. No. 09/404,484, filed Sep. 23, 1999), might be employed. Economical dilution for many independent cells might be achieved, for example, by using a peristaltic pump whose head can accomodate scores or more of individual pumping tubes. One branch of a 'Y' connector or 'mixing T' connector can pull a certain amount from a microreactor (remote from the chamber that will make measurements), while the other branch pulls from a solvent reservoir. The diluted mixture from each reactor is then simultaneously pumped through the sub-chambers in the SMSLS unit. Of course, other pump types and schemes can be used as well.

3. Multiple Sampling From a Reactor

There are situations where it may be desirable to monitor samples from more than one place in a polymer reactor, whether the polymer reaction includes polymerization, degradation, biosynthesis of products, functionalization reactions, batch or sequential copolymerization reactions, etc. It is not economically attractive, nor technologically efficient to have a separate detector device and computer for each place samples are to be withdrawn from.

In some cases a large industrial reactor may exhibit significant spatial heterogeneity, whether due to imperfect convective mixing or stirring, thermal gradients, etc. In such a case, as many reactor sampling sites as desired can be created at different places on or within the reactor, and each one can feed a separate sub-chamber in a single SMSLS device. The output signals can be treated by a single computer, so that a spatial map of how the product evolves in time can be made. This can lead not only to better reactor operation and design, but to a more representative online characterization of product averaged over the tank's volume.

Similar considerations apply for continuous reactors, where product composition is a function of position (and possibly time) in the reactor; sampling can be made from any number of desired points along or within the reactor. Likewise, multi-stage reactors, whether they be for functionalization, different steps in fermentation or processing, etc., can benefit from SMSLS.

4. Multiple Analysis Instruments.

Analytical chemistry laboratories for both synthetic polymers and biopolymers frequently employ separation techniques such as Size Exclusion Chromatography (SEC), Field Flow Fractionation (FFF), gel electrophoresis, etc. These techniques allow the distribution of polymer populations to be determined, and hence frequently used parameters such as number-, weight- and z-averages can also be determined, as well as the existence of any multimodality in the population.

Light scattering has proven to be a powerful tool for analyzing fractionated material as it flows from the separation device.[6] Current light scattering instruments, however, are very expensive, and few laboratories typically can afford to buy more than one or two. Hence, other separation units in the laboratory can only use less powerful, traditional techniques (such as SEC column calibration via molecular mass standards), since a currently available light scattering detector can only be used for one sample at a time from a given separation unit.

In contrast, SMSLS will allow the fractionated flows from many separate separation units (e.g. multiple, individually pumped SEC columns) to be pumped through separate sub-chambers in a single SMSLS unit. The scattered signal output of each detector in this case will most likely be led to the individual computer assigned to each SEC unit. This is one of the cases where it will actually be preferred to use multiple computers with a single SMSLS unit, since each sub-chamber's output will be treated with the other data from other instruments used in each SEC unit. Large cost savings and increase in analytical laboratory throughput are envisioned in this application. The fact that the SMSLS unit will be spatially separated from various separation units in a laboratory, typically by several meters, will not be a problem, since very low dead volume tubing is available, that will add only negligible interdetector dead volume; e.g. standard SEC tubing of inner diameter 0.005" will add only 0.013 milliliters of dead volume per meter of tubing. Typically, an SEC detector can add anywhere from 0.01 to 0.8 milliliters of dead volume in and of itself.

5. Interactions of Polymers and/or Colloids with other Polymers and/or Colloids, Small Molecules, Denaturants, etc.

Polymers and colloids can undergo changes in their interactions, dimensions and degree of association when they interact with other polymers and/or colloids, or other agents, such as denaturants, small molecules, salts, heat, enzymes, etc.

For example, the inventor and his colleagues recently demonstrated that the automatic mixing and dilution technique described in Ser. No. 09/404,484, filed Sep. 23, 1999, could be used to determine how electrically charged polymers (polyelectrolytes) change their dimensions, interactions and hydrodynamic properties in response to continuous changes in the concentration of salt in solution with them.[7] In this method a ternary, programmable mixing pump is used. One of the pump inlets continuously withdraws a fixed percentage (e.g. 10%) of the polyelectrolyte in a stock solution at fixed concentration (e.g. pure water in this case), whereas the second and third pump inlets draw from a pure solvent reservoir (again, water in this case) and a reservoir containing a different solvent (water with a high concentration of sodium chloride or other type of salt in this case), respectively. The pump is programmed so that the mixed solvent continuously varies from being pure solvent to being the different solvent (or vice versa), with all intermediate compositions represented. The output of the pump (at a flow rate generally in the range of 0.1 to 3 ml/minute) hence consists of a fixed concentration of polyelectrolyte existing in a solvent that varies continuously from pure solvent to the different solvent (e.g. high concentration salt water). The pump continuously pumps this solution of changing solvent composition, but fixed polyelectrolyte composition, through the light scattering detector, and, optionally other detectors such as a viscometer and a refractometer. The complete record of how the polyelectrolyte dimensions (mean square radius of gyration $<S^2>$) and interactions ($A_2$, $A_3$, etc.) as well as any strong long-range correlations is automatically recorded. If a viscometer is also included, the record of the polyelectrolyte's hydrodynamic behavior is also monitored.

Other applications can include how proteins or pharmaceutical agents react to other large or small molecules, denaturation of proteins in response to urea and other denaturants, how different polymers react to each others' presence in solution, how surfactants micellize or demicellize with changing surfactant concentration, salt concentration, etc. With SMSLS multiple changing environments can be explored simultaneously. Samples in sub-chambers can be at rest, (either in sub-chambers that directly accept sample by pipetting, etc., or in sample cells that are inserted into sub-chambers), or in flow. The environment can be changed by mixing with the component whose effect is to be explored; e.g. concentrated salt solutions or solutions containing a different polymer or colloid, could be pipetted into sub-chambers to measure their effects. Alternatively, the automatic mixing and dilution technique could be used to continuously change sample composition so that the effects could be measured.

6. Large Scale Equilibrium Characterization of Polymers and Colloids.

Virtually all traditional polymer solution characterization is performed on solutions which are at equilibrium, or thought to be at equilibrium. Although equilibrium properties of polymeric products are often characterized by separation techniques such as SEC, there are instances where such techniques may be impractical, too slow, or prohibitively expensive. For example, polymers may be too large to be separated by columns, or there may not exist columns for separating certain polymers, or the polymers might damage or plug expensive separation columns, or interactions (e.g. $A_2$) must be determined (they are not normally determined in a separation experiment), or it is necessary only to know average quantities of the polymer (e.g. $M_w$) and not the detailed population distribution, or there may simply be too many polymer samples to run per day for slow separation techniques to keep up with. SMSLS can be-of decisive utility in high throughput equilibrium characterization since a complete characterization of $M_w$, $<S^2>_z$ and $A_2$ can be determined with as few as three different concentrations of a sample (or just a single concentration if $A_2$ is negligibly small), and no time is needed for separation (the lack of separation defines this as a 'batch' characterization). With hundreds of sub-chambers available, robots or humans could introduce one or more concentrations of each of hundreds or more polymers to be characterized into one or more sub-chambers. The light scattering measurements needed for the characterization are limited in time only by the rate at which samples can be introduced into the sub-chambers, since the intensity readings can be made in seconds or less. Automated sample preparation by robots would entirely automate the process and lead to characterization rates that are currently inconceivable.

If sub-chambers with flow capability are used it is possible to obtain a complete record of scattering behavior vs. polymer concentration, as was recently demonstrated in an article from the inventor's research group for a single sample light scattering device.[8] In this latter method $M_w$, $A_2$, $A_3$, $<S^2>_z$ and intrinsic viscosity of polymer samples was automatically obtained.

7. Determination of the Dissolution Properties of Dry Polymer Powders

The rate at which dry polymer powders dissolve is often critical to a product's performance; e.g. sometimes a quick dissolution is desired for mixing or processing components (e.g. pectins and flavoring agents), or slow dissolution (gelatin capsules for time released drug activity). The rate of dissolution, in turn, is dependent on many complex factors; polymer molecular weight, lump formation during dissolution, temperature, solvent composition, method of producing the dry powder (precipitation and drying, freeze drying, etc.), milling of powders, etc.

SMSLS can be used to monitor many simultaneous dissolution assays when the techniques of a recently published article of the inventor's research group is used.[9]

8. Characterization of Stable or Evolving Solutions Containing Both Polymers and Colloids.

When an SMSLS device, or certain of its sub-chambers are used with sample flowing through them, it will be possible to apply the method of Heterogeneous Time Dependent Light Scattering (HTDSLS), that is described and claimed in my U.S. Pat. No. 6,052,184, and has recently also been published.[10] In HTDSLS there is a population of polymers that co-exist with large particles such as microgels, microcrystals, bacteria, cell fragments or clusters, etc. These latter produce large spikes of scattered light when they pass through the scattering volume. By electronically recognizing and counting these spikes, and simultaneously recovering the scattering background due to the polymer population, it is possible to characterize the evolution of both the large particle and polymer components of the solution.

Examples include: a microbe degrades a polysaccharide and grows, in which case the decreasing mass and dimensions of the polysaccharide, as well as the increasing number density of bacteria are followed in time; the aggregation of polymer in time, whether due to interactions with itself or some other agent, to form large micro-gels results in an increasing density of spikes, with increasing amplitude, and a decreasing background of polymer.

9. Online Determination of Polydispersity

It is noted that in conjunction with my U.S. Pat. No. 6,052,184, and my recently published article "A Method for Online Monitoring of Polydispersity during Polymerization Reactions"[11], the SMSLS device can be used to add this important dimension of characterization to multiple, simultaneous polymerization reactions. Hence, a polymerization reaction can be started, and during the production of polymer not only are conversion, viscosity and weight averaged molecular mass $M_w$, monitored online, but also the evolution of any polydispersity (broadening or narrowing of the population mass distribution), occurrence of multimodality (e.g. distinct sub-populations). Not only could this capability lead to useful feedback control of polymerization reactions, but there would also be a complete characterization of the polymer by the time the reaction was finished. This would either eliminate or at least lessen the need for post-production analytical determinations of polymer mass distributions.

Further Considerations on Absolute and Relative Scattering Intensity Measurements The system of the present invention can simultaneously measure the light scattered from a plurality of independent samples. With the system of the present invention hundreds of samples can be measured simultaneously. The system of the present invention uses one or more light sources and one or more light detectors to achieve this.

The system of the present invention feeds the signal data from the plurality of samples to a single computer for analysis.

The present invention uses SMSLS, among other things, to make absolute measurements of the weight averaged mass $M_w$ of polymers and colloids, and in some instances also makes absolute determinations of mean squared radius of gyration $<S^2>$, second and third virial coefficients $A_2$ and $A_3$, and in certain cases absolute kinetic constants for time dependent processes are obtained.

The requirements for making such absolute.measurements are:

1) the low light scattering from an absolute reference solvent (e.g. toluene) must be accurately measurable; this requires a sufficiently bright source and high sensitivity detectors;

2) it must be verified that there is not a significant amount of stray light present in the scattering chamber or vial; a method for doing this was set out in Florenzano, Strelitzki and Reed (referenced herein); normally, significant stray light cannot be avoided when uncollimated or unfocused, diffuse light sources are used;

3) Either a highly stable light source must be used (e.g. a stabilized laser or lamp), or account must be taken of intensity swings in the light source during measurements (e.g. using a beam splitter to pick off a reference portion of the light source and dividing all measurements by the simultaneous picked-off value);

4) The light scattering medium must be optically transparent; the entire absolute technique of Zimm and others (referenced herein) is predicated on the assumption that the majority of scattered photons reaching the photodetector(s) have scattered only once. In fact, the majority of incident photons don't scatter at all, and there is generally little or no measurable change in transmittance above the pure solvent level when polymers are present in the solvent.

Usually, optical transparency of say, over 90% transmission over the length of the scattering cell will guarantee that the majority of scattering events are single scattering events.

The entire absolute characterization technique is predicated on single scattering (as mentioned in U.S. Pat. No. 6,052,184).

In summary of this issue, the present invention comprises an SMSLS device capable of absolute macromolecular characterization.

The applications mentioned above that preferably use absolute macromolecular characterization are:

2. High throughput screening in polymer synthesis
3. Multiple sampling from a reactor
4. Multiple analysis instruments.
5. Interactions of polymers and/or colloids with other polymers and/or colloids, small molecules, denaturants, etc.
6. Large scale equilibrium characterization of polymers and colloids.
8. Characterization of stable or evolving solutions containing both polymers and colloids.
9. Online determination of polydispersity The method of the present invention uses fill mode and flow mode for the device, in addition to a vial insert mode.

The present invention can also make relative intensity measurements in the single scattering regime, for which the requirements are less stringent than for measurement of absolute scattering; namely, it is not required that the scattering intensities be related to an absolute standard (such as toluene), and more stray light can usually be tolerated. The following are some applications where relative scattering intensity measurements can be useful.

1. Large scale parallel testing of solution stability. The onset of instability can be sensitively followed in the dilute, single scattering regime long before a solution becomes cloudy or otherwise passes into a highly scattering regime.
2. High throughput screening in polymer synthesis where it is desired to know if polymerization is occurring at all, and if so, what the relative change in polymer mass is during synthesis, and what the relative kinetic rates are.
3. Multiple sampling from a reactor Useful where spatial or temporal heterogeneity in reactors is to be followed, and/or where relative changes in mass, kinetics, etc. might be useful without a full, absolute characterization.
5. Interactions of polymers and/or colloids with other polymers and/or colloids, small molecules, denaturants, etc. When it is desired to know if any interactions are taking place at all, and if so, what the relative changes in interaction parameters, mass, size, etc. may be.
7. Determination of the dissolution properties of dry polymer powders
8. Characterization of stable or evolving solutions containing both polymers and colloids.

The following is purely illustrative. One way to express the range of concentration and particle mass is as follows: Neglecting interparticle effects ($A_2$, $A_3$, etc.) and the angular dependence of light scattered (i.e. restricting to particles that are several times less than the wavelength of light and) we have that $$KcM_{w=I}$$

where $M_w$ is the weight averaged molecular mass of the polymer, c is the concentration of polymer in solution (g/cm$^3$), I is the absolute scattered-intensity of light (expressed as the Rayleigh ration, units of cm$^{-1}$, and obtained by relating the relative scattering voltage of a sample to the scattering voltage of an absolute standard such as toluene), and K is an optical constant given, for vertically incident polarized light, by $$K = \frac{4(\pi n^2 (dn/dc))^2}{N_A \lambda^4}$$

when n is the index of refraction of the solvent, $N_A$ is Avogadro's number (6.02×10$^{23}$ mole$^{-1}$), $\lambda$ is the vacuum wavelength of the incident light, and dn/dc is the incremental index of refraction the polymer in the solvent (cm$^3$/g).

Typically a light scattering unit designed for single scattering detection can measure I down to about 10$^{-6}$ cm$^{-1}$ with reasonable accuracy, and possibly to 10$^{-7}$, although the absolute lower limit of $M_w$ and c measurable is limited currently only by continuing improvements in detector sensitivity and signal/noise ratio. At the upper end, when I becomes roughly of the order of 0.01, single scattering will still predominate.

For a 677 nm vertically polarized laser, a 1 cm pathlength cell, and a typical dn/dc~0.15 (K~10$^{-7}$) for a water soluble polymer, and a lower I=10$^{-7}$, M=500 g/mole could be measured at a concentration of 0.002 g/cm$^3$. At the other extreme, multiple scattering would start to become noticeable at about I=0.01, in which case a polymer of M=10$^6$ g/mole might be measured up to a concentration of 0.1 g/cm$^3$ and still be in the single scattering regime.

A bank of lasers is an example of a device comprising a plurality of sources of collimated light.

By collimated is meant practically, not perfectly, collimated, as most commercial lasers emit practically collimated light (i.e., typical commercial lasers emit light that has a relatively small divergence angle, thought it appears to be collimated).

PARTS LIST

The following is a list of parts and materials suitable for use in the present invention:

10 SMSLS apparatus of a preferred embodiment of the present invention
15 SMSLS substrate for chambers and laser 20
20 laser, such as a 25 milliwatt, vertically polarized, 677 nanometer wavelength diode laser from Laser Max, Inc.
21 laser beam
22 split laser beams
23 split laser beams.from split laser beams 22
30 computer such as a Dell with Pentiun II, 350 MHz
31 wires electronically connecting array 61 to computer 30
32 wires electronically connecting array 62 to computer 30
33 wires electronically connecting photodetectors 55 to a signal processing circuit (e.g. Data Translation Inc., DT2808 Analog to Digital converter)
40 block containing series chambers 41
41 chambers (such as hollow open-top cavities formed in blocks 40, 45)
42 light entry port 43 light detecting means exit ports in block 40
44 block containing series chambers 41
45 block containing parallel chambers 41
46 block containing parallel/series chambers 41
47 block containing parallel/series chambers 41
48 block containing series chambers 41
49 block containing series chambers 41
50 typical SMSLS device in parallel-mode
51 optical fibers to photodetectors
52 detector plate
55 photodetectors such as Hamnnamatsu S1406 photodiodes
59 beam dump (optional)
60 typical SMSLS device in parallel/series mode
61 light detector array (such as photodiodes or charge coupled devices)
61 light detector array, such as a box containing photodetectors and signal processing electronics; alternatively, the signal processing electronics can be installed inside the computer
70 SMSLS device in mixed parallel/series mode
71 beam splitters, such as those available from Edmund Scientific or Newport Corp.
80 SMSLS device in insertion series mode
90 block containing index-matched insertion wells 91
91 index-matched insertion wells
92 cylindrical sample-containing insertion cuvette to insert in wells 91
93 block containing flow-through chambers 94
94 flow-through chambers
95 fittings for receiving stainless steel or plastic tubing (e.g. such as is used in High Pressure Liquid Chromatography practice)
96 light passageways to light detectors
100 SMSLS device in flow-through series mode
101 through bolts
102 through bolt nuts
103 sample wells
104 end plates
105 transparent dividers between wells (e.g., microscope cover slips)
106 transparent side plate (e.g., microcope slide)
107 clamping side plate with holes for fibers or directly to side-mounted photodetectors
108 holes for fibers or directly to side-mounted photodetectors in clamping side plate 107
109 main body
110 hole for laser bean running through all cells
120 non-collimated polychromatic light source (there could be a wavelength filter—not shown—over light source 120)
131 wires electronically connecting array 161 to computer 30
140 block containing chamber 141
141 chambers (such as hollow open-top cavity formed in block 140) with multi-angle detection
145 wavelength bandpass filter
146 block containing chamber 147
147 chamber for containing liquid or a holder containing liquid
148 block containing chamber 149
149 chamber for containing liquid or a holder containing liquid
150 series-mode chamber
160 laser (though it could instead be a photodiode, laser diode, light bulb, or other source of light useful in light scattering detection)
161 light detector array (such as CCDs)
162 focusing lens assembly
163 collimating lens assembly
164 partially focusing lens assembly
165 focusing lens assembly
170 parallel-mode SMSLS device
180 parallel-mode SMSLS device
196 light passageways to light detectors All references mentioned herein are incorporated herein by reference.

All measurements disclosed herein are at standard temperature and pressure, at sea level on Earth, unless indicated otherwise. All materials used or intended to be used in a human being are biocompatible, unless indicated otherwise.

The following references are incorporated herein by reference:

1) Florenzano, F. H.; Strelitzki, R.; Reed, W. F. "*Absolute Online Monitoring of Molar Mass during Polymerization Reactions*", Macromolecules, vol. 31, no. 21, 7226–7238, 1998;
2) Reed, C. E. and Reed, W. F. "*Light Scattering Power of Randomly Cut Random Coils with Application to the Determination of Depolymerization Rates*", J. Chemical Physics, 91, 7193–7199, 1989;
3) W. F. Reed, C. E. Reed and L. Byers, "*Random Coil Scission Rates Determined by Time Dependent Total Intensity Light Scattering: Hyaluronate Depolymerization by Hyaluronidase*", Biopolymers, vol. 30, 1073–1082, 1990;
4) S. Ghosh and W. F. Reed "*New Light Scattering Signatures from Polymers undergoing Depolymerization with Application to Proteoglycan Monomer Degradation*", Biopolymers, 5, 435–450, 1995;
5) W. F. Reed, "*Time dependent light scattering from single and multiply stranded linear polymers undergoing random and endwise scission*", J. Chem. Phys., 103, 7576–7584, 1995;
6) ACS symposium series 635 "*Strategies in Size Exclusion Chromatograpy*", Ed. M. Potschka and P. Dubin, 1996;
7) E. Bayly, J. L. Brousseau and W. F. Reed, "*Continuous Monitoring of the Effect of Changing Solvent Conditions on Polyelectrolyte Conformations and Interactions*", accepted July 2000 by Int. J. of Polymer Characterization and Analysis;
8) R. Strelitki and W. F. Reed, "*Automated Batch Characterization of Polymer Solutions by Static Light Scattering and Viscometry*", J. App. Polym. Sci., 73, 2359–2368, 1999
9) R. Michel and W. F. Reed, "*New Evidence for the Non-equilibrium Nature of the "Extraordinary Diffusional Phase" in Polyelectrolyte Solutions*" Ricardo de Cunha Michel and W. F. Reed, Biopolymers, 53, 19–39, 2000;
10) R. Schimanowski, R. Strelitzki, D. Mullin and W. F. Reed, "*Heterogeneous Time Dependent Static Light Scattering*", Macromolecules, 32, 21, pp 7055–7063, 1999; and 11) W. F. Reed, "A Method for Online Monitoring of Polydispersity during Polymerization Reactions", Macromolecules, vol. 33, pp. 7165–7172, 2000.

The foregoing embodiments are presented by way of example only; the scope of the present invention is to be limited only by the following claims.

What is claimed is:

1. Apparatus including a light scattering device for conducting simultaneous multi-sample light scattering comprising:
   a) a source of collimated, focused, or partially focused light;
   b) at least two sub-chambers, each of which can hold an independent liquid sample comprising a solution containing polymers and/or colloids, and each of which can be irradiated by incident light from the source of collimated, focused, or partially focused light, the light scattered by the sample in each of which is detected for analysis;
   c) light detection means sensitive enough to detect single scattering from the samples, the light detection means being optically coupled to the sub-chambers; and
   d) means for determining at least one of the following characteristics of the polymers and/or colloids in the liquid samples: relative mass; absolute mass; spatial dimensions; sizes; shapes; interactions; concentration; and hydrodynamic properties.

2. The apparatus of claim 1, further comprising a computer.

3. The apparatus of claim 1, wherein the light source is a laser.

4. The apparatus of claim 1, wherein the incident light is delivered to the sub-chambers in series from a single light source.

5. The apparatus of claim 1, wherein the light source is split and delivered to each sub-chamber, the light being collimated or focused, or to a subset of sub-chambers (i.e. purely in parallel, or partially in parallel and partially in series).

6. The apparatus of claim 1, comprising a plurality sources, each of which is incident upon one or more sub-chambers.

7. The apparatus of claim 1, further comprising one or more detection means placed at angles from 2° up to 178° from the incident beam direction for each sub-chamber.

8. The apparatus of claim 1, further comprising means for performing simultaneously relative or absolute molecular weight characterization of independent liquid samples containing polymers or colloids.

9. The apparatus of claim 1, further comprising means for simultaneously making relative or absolute intensity, or relative or absolute molecular weight characterization of independent liquid samples from separate polymer reactions.

10. The apparatus of claim 9, wherein the polymer reaction is a polymerization reaction.

11. The apparatus of claim 9, wherein the polymer reaction is a polymer degradation reaction.

12. The apparatus of claim 9, wherein the polymer reaction is an interaction with small molecules, other polymers, colloids or microbes.

13. The apparatus of claim 9, wherein the polymer reaction is dissolution of a dry powder in a solvent.

14. The apparatus of claim 9, further comprising means for analyzing by a single computer the photodetector outputs from the scattering from the independent liquid samples.

15. The apparatus of claim 9, further comprising means for analyzing by a single computer the scattering from the independent liquid samples.

16. The apparatus of claim 9, further comprising means for analyzing by a single computer the photodetector outputs from the scattering from the independent samples.

17. The apparatus of claim 9, further comprising means for analyzing by more than one computer the scattering from the independent samples.

18. The apparatus of claim 9, further comprising means for flowing the independent liquid samples into the sub-chambers.

19. The apparatus of claim 1, wherein large or detector-saturating scattering signals are used to identify and characterize instability in solutions containing polymers and/or colloids.

20. The apparatus of claim 1, wherein the independent liquid samples can come from a plurality of separate chemical analysis devices.

21. The apparatus of claims 20, wherein at least one of the separate chemical analysis devices is selected from the group consisting of size exclusion chromatography columns, field flow fractionation devices, refractive index detectors, viscosity detectors, ultraviolet and visible spectrophotometers, and conductivity detectors.

22. The apparatus of claim 1, further comprising means for allowing the samples to be introduced into the sub-chambers by a pipette, syringe, syringe pump, peristaltic pump, or other transfer device, either manually or by a robotic device, and remain, without flow, during the measurements.

23. The apparatus of claim 1, further comprising flow fittings so that at least some of the sub-chambers can be independently filled by a flowing liquid, either at intervals or in a continuous fashion.

24. The apparatus of claim 1, further comprising means for allowing the individual sub-chambers to accept sample cells containing sample fluid.

25. The apparatus of claim 24, wherein an index matching fluid can be used to optically couple the individual sample cells inserted into each sub-chamber.

26. The apparatus of claim 1, wherein the light source produces collimated or focused light.

27. The apparatus of claim 1, further comprising a non-collimated light source.

28. The apparatus of claim 1, further comprising a separate source of light for each sub-chamber.

29. The invention of claim 1, whereby the polydispersity of an evolving polymerization reaction is monitored online in one or more of the sub-chambers.

30. The invention of claim 1, wherein at least one optical fiber coupled to a light detector is in direct physical contact with liquid in the sub-chamber.

31. The apparatus of claim 1, further comprising means for monitoring changes in at least one of the following characteristics of the polymers and/or colloids in the liquid sample solutions: relative mass; absolute mass; spatial dimensions; sizes; shapes; interactions; concentrations; and hydrodynamic properties.

32. Apparatus including a light scattering device for conducting simultaneous multi-sample light scattering comprising:
   a) a source of collimated or focused light;
   b) at least two sub-chambers, each of which can hold an independent liquid sample comprising a solution containing polymers and/or colloids, and each of which can be simultaneously irradiated by incident light from the source of collimated or focused light, the light scattered by the sample in each of which is detected for analysis;

c) light detection means optically coupled to the sub-chambers; and d) means for determining at least one of the following characteristics of the polymers and/or colloids in the liquid samples: relative mass; absolute mass; spatial dimensions; sizes; shapes; interactions; concentration; and hydrodynamic properties.

33. The apparatus of claim 32, further comprising means for monitoring changes in at least one of the following characteristics of the polymers and/or colloids in the liquid sample solutions: relative mass; absolute mass; spatial dimensions; sizes; shapes; interactions; concentrations; and hydrodynamic properties.

34. Apparatus including a light scattering device for conducting simultaneous multi-sample light scattering comprising:

a) a lighting device comprising a plurality of sources of collimated or focused light;

b) at least two sub-chambers, each of which can hold an independent liquid sample comprising a solution containing polymers and/or colloids and each of which can be simultaneously irradiated by incident light from the lighting device, the light scattered by the sample in each of which is detected for analysis;

c) light detection means optically coupled to the sub-chambers; and d) means for determining at least one of the following characteristics of the polymers and/or colloids in the liquid samples: relative mass; absolute mass; spatial dimensions; sizes; shapes; interactions; concentration; and hydrodynamic properties.

35. The apparatus of claim 34, further comprising means for monitoring changes in at least one of the following characteristics of the polymers and/or colloids in the liquid sample solutions: relative mass; absolute mass; spatial dimensions; sizes; shapes; interactions; concentrations; and hydrodynamic properties.

36. Apparatus including a light scattering device for conducting simultaneous multi-sample light scattering comprising:

a) a source of collimated or focused light;

b) at least two sub-chambers, each of which can hold an independent liquid sample comprising a solution containing polymers and/or colloids, and each of which can be irradiated by incident light from the source of collimated or focused light, the light scattered by the sample in each of which is detected for analysis;

c) light detection means sensitive enough to detect single scattering from the samples, the light detection means being optically coupled to the sub-chambers;

d) a computer for analyzing data from the light detection means; and e) means for determining at least one of the following characteristics of the polymers and/or colloids in the liquid samples: relative mass; absolute mass; spatial dimensions; sizes; shapes; interactions; concentration; and hydrodynamic properties.

37. The apparatus of claim 36, further comprising means for monitoring changes in at least one of the following characteristics of the polymers and/or colloids in the liquid sample solutions: relative mass; absolute mass; spatial dimensions; sizes; shapes; interactions; concentrations; and hydrodynamic properties.

38. Apparatus for conducting simultaneous multi-sample light scattering comprising:

(a) a plurality of chamber means, for containing liquid samples containing polymers and/or colloids, in which single light scattering can occur;

(b) light source means for providing collimated, focused, or partially focused light to be scattered to the chamber means;

(c) light detectors optically coupled to the chamber means for detecting scattered light, the light detectors being sensitive enough to detect single scattering from the chambers; and (d) transmission means for transmitting information from the light detectors to a computer for analysis; and (e) means for determining at least one of the following characteristics of the polymers and/or colloids in the liquid samples: relative mass; absolute mass; spatial dimensions; sizes; shapes; interactions; concentration; and hydrodynamic properties.

39. The apparatus of claim 38, wherein the information from all light detectors is transmitted to a single computer.

40. The apparatus of claim 38, further comprising means for monitoring changes in at least one of the following characteristics of the polymers and/or colloids in the liquid sample solutions: relative mass; absolute mass; spatial dimensions; sizes; shapes; interactions; concentrations; and hydrodynamic properties.

41. A method of performing simultaneous multi-sample light scattering, comprising:

(a) providing a plurality of chamber means in which light scattering can occur;

(b) placing liquid samples containing polymers and/or colloids in the chamber means;

(c) providing collimated, focused, or partially focused light to be scattered to the chamber means;

(d) detecting light scattered in the chamber means with light detectors optically coupled to the chamber means, the light detectors being sensitive enough to detect single scattering from the chambers; and (e) transmitting information from the light detectors to a computer for analysis.

42. The method of claim 41, wherein the information from the light detectors is transmitted to a single computer.

43. The method of claim 41, wherein light is provided by a laser.

44. The method of claim 41, further comprising simultaneously making relative or absolute molecular weight characterization of independent liquid samples from separate polymer reactions.

45. The method of claim 44, wherein the polymer reaction is a polymerization reaction.

46. The method of claim 44, wherein the polymer reaction is a polymer degradation reaction.

47. The method of claim 44, wherein the polymer reaction is the dissolution of the dry polymer in a solvent.

48. The method of claim 44, wherein the polymer reaction is an interaction with small molecules, other polymers, colloids or microbes.

49. The method of claim 41, wherein large or detector-saturating scattering signals are used to identify and characterize instability in solutions containing polymers and/or colloids.

50. The method of claim 41, wherein the liquid samples contain polymers and/or colloids, and further comprising determining at least one of the following characteristics of the polymers and/or colloids in the liquid samples: relative mass; absolute mass; spatial dimensions; sizes; shapes; interactions; concentrations; and hydrodynamic properties.

51. A method of performing simultaneous multi-sample light scattering, comprising:
   (a) providing a plurality of chamber means in which light scattering can occur;
   (b) placing liquid samples containing polymers and/or colloids in the chamber means;
   (c) providing collimated, focused, or partially focused light to be scattered to the chamber means from a single light source; and
   (d) detecting light scattered in the chamber means with light detectors optically coupled to the chamber means.

52. The method of claim 51, wherein a computer is used to analyze the scattered light.

53. The method of claim 51, wherein the light source is a laser.

54. The method of claim 51, wherein the liquid samples contain polymers and/or colloids, and further comprising determining at least one of the following characteristics of the polymers and/or colloids in the liquid samples: relative mass; absolute mass; spatial dimensions; sizes; shapes; interactions; concentrations; and hydrodynamic properties.

55. A method of performing simultaneous multi-sample light scattering, comprising:
   (a) providing a plurality of chamber means in which light scattering can occur;
   (b) placing liquid samples containing polymers and/or colloids in the chamber means;
   (c) providing light to be scattered to the chamber means from a device comprising a plurality of sources of collimated or focused light; and
   (d) detecting light scattered in the chamber means with light detectors optically coupled to the chamber means.

56. The method of claim 55, wherein the liquid samples contain polymers and/or colloids, and further comprising determining at least one of the following characteristics of the polymers and/orcolloids in the liquid samples: relative mass; absolute mass; spatial dimensions; sizes; shapes; interactions; concentrations; and hydrodynamic properties.

57. A method of performing simultaneous multi-sample light scattering, comprising:
   (a) providing a plurality of chamber means in which light scattering can occur;
   (b) placing liquid samples containing polymers and/or colloids in the chamber means;
   (c) providing collimated, focused, or partially focused light to be scattered to the chamber means;
   (d) detecting light scattered in the chamber means with light detectors optically coupled to the chamber means, the light detectors being sensitive enough to detect single scattering from the chamber means; and
   (e) transmitting information from the light detectors to a single computer for analysis.

58. The method of claim 57, wherein the liquid samples contain polymers and/or colloids, and further comprising determining at least one of the following characteristics of the polymers and/or colloids in the liquid samples: relative mass; absolute mass; spatial dimensions; sizes; shapes; interactions; concentrations; and hydrodynamic properties.

59. A method of performing simultaneous multi-sample light scattering, including:
   providing a light scattering chamber consisting of two or more sub-chambers;
   receiving an independent liquid sample solution in at least two of the sub-chambers;
   irradiating each sub-chamber having an independent sample solution with incident collimated, focused, or partially focused light;
   detecting the light scattered by the sample in each sub-chamber with light detector means sensitive enough to detect single scattering from the sub-chambers.

60. The method of claim 59, wherein the incident light is delivered to the sub-chambers in series.

61. The method of claim 59, wherein the light source is split and delivered to each sub-chamber, the light being collimated or focused, or to a subset of sub-chambers (i.e. purely in parallel, or partially in parallel and partially in series).

62. The method of claim 59, further comprising providing a plurality of light sources, each of which is incident upon one or more sub-chambers.

63. The method of claim 59, further comprising placing one or more detection means at angles from 2° up to 178° from the incident beam direction for each sub-chamber.

64. The method of claim 59, further comprising placing one or more detection means at angles from 5° up to 175° from the incident beam direction for each sub-chamber.

65. The method of claim 59, further comprising placing one or more detection means at angles from 20° up to 160° from the incident beam direction for each sub-chamber.

66. The method of claim 59, further comprising placing one or more detection means at angles from 30° up to 150° from the incident beam direction for each sub-chamber.

67. The method of claim 59, further comprising performing simultaneously relative or absolute molecular weight characterization of independent liquid samples containing polymers or colloids.

68. The method of claim 67, wherein the independent liquid samples can come from a plurality of separate chemical analysis devices.

69. The method of claim 68, wherein at least one of the separate chemical analysis devices is selected from the group consisting of: size exclusion chromatography columns, field flow fractionation devices, refractive index detectors, viscosity detectors, ultraviolet and visible spectrophotometers, and conductivity detectors.

70. The method of claim 67, further comprising analyzing by a single computer the photodetector outputs from the scattering from the independent liquid samples.

71. The method of claim 67, further comprising analyzing by a single computer the scattering from the independent liquid samples.

72. The method of claim 67, further comprising analyzing by a single computer the photodetector outputs from the scattering from the independent liquid samples.

73. The method of claim 67, further comprising analyzing by more than one computer the scattering from the independent liquid samples.

74. The method of claim 67, further comprising introducing the liquid samples into the sub-chambers by a pipette, syringe or other transfer device, either manually or by a robotic device, and remain, without flow, during the measurements.

75. The method of claim 67, wherein the independent liquid samples are flowed into the sub-chambers.

76. The method of claim 59, further comprising providing flow fittings so that each sub-chamber can be independently filled by a flowing liquid.

77. The method of claim 59, further comprising allowing the individual sub-chambers to accept sample cells containing sample fluid.

78. The method of claim 59, wherein an index matching fluid can be used to optically couple the individual sample cells inserted into each sub-chamber.

79. The method of claim 59, wherein a collimated or focused light source is used.

80. The method of claim 59, wherein a non-collimated light source is used.

81. The method of claim 59, wherein a separate source of light is used for each sub-chamber.

82. The method of claim 59, wherein the liquid samples contain polymers and/or colloids, and further comprising determining at least one of the following characteristics of the polymers and/or colloids in the liquid samples: relative mass; absolute mass; spatial dimensions; sizes; shapes; interactions; concentrations; and hydrodynamic properties.

* * * * *